United States Patent [19]

Morrison et al.

[11] Patent Number: 5,593,833
[45] Date of Patent: Jan. 14, 1997

[54] ASSESSMENT OF ALLELIC VARIATION IN VITAMIN D RECEPTOR CORRELATED TO BONE DENSITY OR TURNOVER

[75] Inventors: Nigel A. Morrison, Pagewood; John A. Eisman, Lindfield; Paul J. Kelly, Waverly, all of Australia

[73] Assignee: Garvan Institute of Medical Research, Darlinghurst, Australia

[21] Appl. No.: 379,496

[22] PCT Filed: Aug. 2, 1993

[86] PCT No.: PCT/AU93/00394

§ 371 Date: Mar. 2, 1995

§ 102(e) Date: Mar. 2, 1995

[87] PCT Pub. No.: WO94/03633

PCT Pub. Date: Feb. 17, 1994

[30] Foreign Application Priority Data

Jul. 31, 1992 [AU] Australia ................... PL3893

[51] Int. Cl.⁶ ............... C12Q 1/68; C12P 19/34; C07H 21/02; C07H 21/04
[52] U.S. Cl. ............... 435/6; 435/91.2; 536/24.3; 536/24.31; 536/24.32; 536/24.33
[58] Field of Search ................... 435/6, 91.2; 536/24.3, 536/24.31, 24.32, 24.33

[56] References Cited

U.S. PATENT DOCUMENTS

| 4,683,202 | 7/1987 | Mullis | 435/91 |
| 5,260,199 | 11/1993 | DeLuca et al. | 435/69.1 |

FOREIGN PATENT DOCUMENTS

| 5776086 | 4/1986 | Australia. |
| 6212790 | 9/1990 | Australia. |
| 8808457 | 11/1988 | WIPO. |
| 9312133 | 6/1993 | WIPO. |

OTHER PUBLICATIONS

Morrison et al, (Mar. 1992), "Frequent alleles of the human vitamin D receptor gene are functionally distinct", J. Cell. Biochem. (Supplement 16C):20, abstract L131.

Baker et al, (1988), "Cloning and expression of full-length cDNA encoding human vitamin D receptor", Proc. Natl. Acad. Sci. 85:3294–3298.

Malloy et al, (1989), "Abnormal binding of vitamin D receptors to deoxyribonucleic acid in a kindred with vitamin D dependent rickets, Type II", J. Clin. Endocrinol. Metabol. 68(2):263–269.

Morrison et al, (1994), "Prediction of bone density from vitamin D receptor alleles", Nature 367:284–287.

Morrison et al., Proc. Natl. Acad. Sci. USA, vol. 89, 1992, pp. 6665–6669.

Bortell et al., Proc. Natl. Acad. Sci. USA, vol. 90, 1993, pp. 2300–2304.

McDonell et al., Molecular Edocrinology, 3(4), 1989, pp. 635–644.

Demay et al., Molecular Endocrinology, 6(4), 1992, pp. 557–562.

Shewey et al., Journal of Immunology, 148(4), 1992, pp. 1265–1273.

Bortell et al., Proc. Natl. Acad. Sci. USA, 89, 1992, pp. 6119–6123.

Primary Examiner—W. Gary Jones
Assistant Examiner—Jeffrey Fredman
Attorney, Agent, or Firm—Rothwell, Figg, Ernst & Kurz

[57] ABSTRACT

The present invention provides a genetic test for assaying predisposition to and/or resistance to high rates of bone turnover, development of low bone mass and responsiveness or otherwise to therapeutic modalities. This is a specific model for use in prediction of osteoporosis and likely response to preventive or therapeutic modalities. It is a general model of allelic variation in transcriptional regulators determining physiological set-points and thus susceptibility or resistance to certain pathophysiological states.

7 Claims, 17 Drawing Sheets

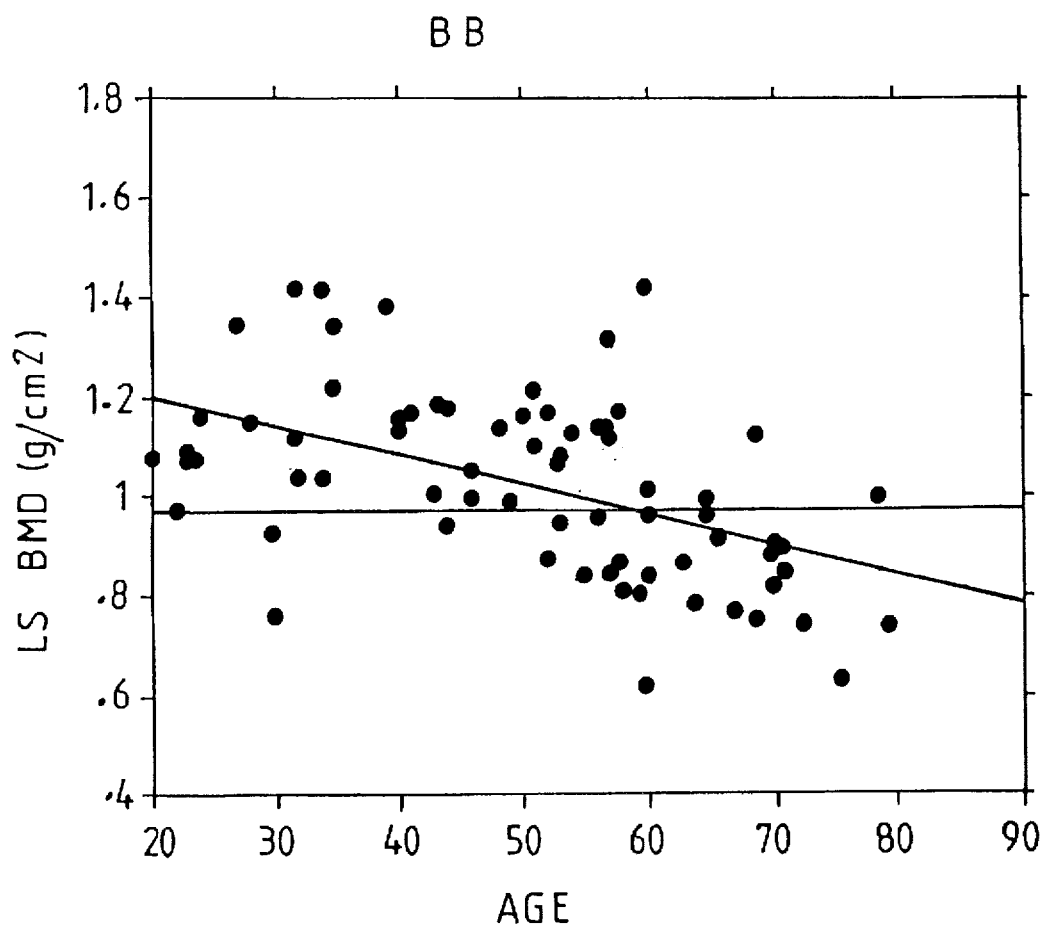
BB
INTERCEPT = 60y
LS BMD = 1.33 − 0.006 age
r = −0.52
p = 0.0001
$\overline{III}.5A$ INTERCEPT = 68y LS BMD = 1.45 − 0.007 age r = −0.51 p = 0.0001

INTERCEPT = 68 y y = -.007x + 1.174 r2 = .349

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 2169 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
CAACCAAGAC TACAAGTACC GCGTCAGTGA CGTGACCAAA GGTATGCCTA GACTCCACCT      60
CCTGGGGAGT CTTTTTCAGC TCCCAGATTC TGGCTCCACC CGTCCTGGGG TTTGGCTCCA     120
ATCAGATACA TGGGAGGGAG TTAGGCACCA ACAGGGAGAG AAGGGCGAGG GTCAGACCCA     180
TGGGGTTGGA GGTGGGTGGG CGGCTCCTCA GCTCTTGCCC GCAGTACCTG GCCATTGTCT     240
CTCACAGGCC GGACACAGCC TGGAGCTGAT TGAGCCCCTC ATCAAGTTCC AGGTGGGACT     300
GAAGAAGCTG AACTTGCATG AGGAGGAGCA TGTCCTGCTC ATGGCCATCT GCATCGTCTC     360
CCCAGGTATG GGGCCAGGCA GGGAGGAGCT CAGGGACCTG GGGAGCGGGG AGTATGAAGG     420
ACAAAGACCT GCTGAGGGCC AGCTGGGCAA CCTGAAGGGA GACGTAGCAA AAGGAGACAC     480
AGATAAGGAA ATACCTACTT TGCTGGTTTG CAGAGCCCCT GTGGTGTGTG GACGCTGAGG     540
TGCCCCTCAC TGCCCTTAGC TCTGCCTTGC AGAGTGTGCA GGCGATTCGG TAGGGGGGAT     600
TCTGAGGAAC TAGATAAGCA GGGTTCCTGG GGCCACAGAC AGGCCTGCGC ATTCCCAATA     660
CTCAGGCTCT GCTCTTGCGT GAACTGGGCT CAACATTCCT GTTATTTGAG GTTTCTTGCG     720
GGCAGGGTAC AAAACTTTGG AGCCTGAGAG ATGGTTCTGC CTATATAGTT TACCTGATTG     780
ATTTTGGAGG CAATGTGCAG TGACCCTTGA CCTCTTCCGC TGGTTAGAGG TGAGAAGAGG     840
GAGAAAAGGC CGAAGAGAAG TTATTGTGAC CTTGGGACAT GATGTCGGTG ATGAGGTCCA     900
AAGAGGGGCG GCCCTGCCTC AGCCTGTGCT AGTGGCCTGT GCCCAGGGAT GCTTTCCTGG     960
ACTGGAGGCT CAAGGAATGG AGATGGCTCC TCTACCCCTG CCCAGCCAGC CTTCTCTCAT    1020
TCATTCATCC ACTTAGCAAC AATTTATTGA GCACCTATTA GGTACCAGGC ACTATGCTAG    1080
GTACTGGGGT TCAGCAGCAA ATGGGACACA GGCTCCTCTC CCATGAAGCT TAGGAGGAAA    1140
CATTAAACAA ATGTTATTTA ATTATTAATT CCTAACAAGG CAAGAGTTTT AAAAATAAAG    1200
TAAGTGATGC TACAGAAGGG TAGAATAGAA GGAGGGAAGC TGACGTGGTC TGGGCTACAG    1260
AGGTAGAGTG TTGCCAGGAA TGGCCTTTTG GAGGAAGACC TTTTGAGCTG TTATCCAAAG    1320
GATCAGTAAG AGTCTGGCAA AGATAGCAGA GCAGAGTTCC AAGCAGAGGG AGCACAGATG    1380
```

```
TGAAGGCTGG  TGGCAGAGAG  CATGGCGCAT  CGGGTCGCTG  AGGGATGGAC  AGAGCATGGA    1440
CAGGGAGCAA  GGCCAGGCAG  GGACAGGGCC  AGGTGCGCCC  ATGGAAGGAC  CTAGGTCTGG    1500
ATCCTAAATG  CACGGAGAAG  TCACTGGAGG  GCTTTGGGGC  CAGGCAGTGG  TATCACCGGT    1560
CAGCAGTCAT  AGAGGGGTGG  CCTAGGGGGT  GCTGCCGTTG  AGTGTCTGTG  TGGGTGGGGG    1620
GTGGTGGGAT  TGAGCAGTGA  GGGGCCCAGC  TGAGAGCTCC  TGTGCCTTCT  CTACTCCCGT    1680
GCCCACAGAT  CGTCCTGGGG  TGCAGGACGC  CGCGCTGATT  GAGGCCATCC  AGGACCGCCT    1740
GTCCAACACA  CTGCAGACGT  ACATCCGCTG  CCGCCACCCG  CCCCCGGGCA  GCCACCTGCT    1800
CTATGCCAAG  ATGATCCAGA  AGCTAGCCGA  CCTGCGCAGC  CTCAATGAGG  AGCACTCCAA    1860
GCAGTACCGC  TGCCTCTCCT  TCCAGCCTGA  GTGCAGCATG  AAGCTAACGC  CCCTTGTGCT    1920
CGAAGTGTTT  GGCAATGAGA  TCTCCTGACT  AGGACAGCCT  GTGCGGTGCC  TGGGTGGGGC    1980
TGCTCCTCCA  GGGCCACGTG  CCAGGCCCGG  GGCTGGCGGC  TACTCAGCAG  CCCTCCTCAC    2040
CCGTCTGGGG  TTCAGCCCCT  CCTCTGCCAC  CTCCCCTATC  CACCCAGCCC  ATTCTCTCTC    2100
CTGTCCAACC  TAACCCCTTT  CCTGCGGGCT  TTTCCCCGGT  CCCTTGAGAC  CTCAGCCATG    2160
AGGAGTTGC                                                                 2169
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:2:

```
CAACCAAGAC  TACAAGTACC  GCGTCAGTGA                                          30
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:3:

```
AACCAGCGGA  AGAGGTCAAG  GG                                                  22
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:4:

CAGAGCATGG ACAGGGAGCA AG    22

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:5:

GCAACTCCTC ATGGCTGAGG TCTCA    25

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:6:

AGGCCTGCRC ATTCCC    16

( 2 ) INFORMATION FOR SEQ ID NO:7:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:7:

GAGGKGCCCA GCTG    14

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:8:

GCGCTGATYG AGGCC 15

ASSESSMENT OF ALLELIC VARIATION IN VITAMIN D RECEPTOR CORRELATED TO BONE DENSITY OR TURNOVER

FIELD OF THE INVENTION

The present invention relates to a method of identifying allelic differences in trans-acting factors as a means of identifying individuals at risk to suffer from an adverse pathophysiological condition. The method of the present invention is particularly useful in assessing allelic variations in the vitamin D receptor gene and thereby predicting predisposition to low or high bone density. Moreover these variants could be used to predict long-term risk of osteoporosis as well as predicting response to different modalities of therapy. This effect is also a model of determination of predisposition to or resistance to other pathological or physiological variations due to other transcription factor gene variants and thus determining risk of disease and of response to therapy. Such transcriptional regulators could be, but are not limited to, ligand-activated gene regulators, such as the steroid/retinoid/thyroid hormone receptor gene family.

BACKGROUND TO THE INVENTION

Vitamin D functions as a potent regulator of bone and calcium homeostasis as well as of cellular differentiation and replication in many target tissues. It acts as its dihydroxylated metabolite (1,25-dihydroxyvitamin D, or calcitriol) through the highly specific vitamin D receptor (1). This trans-acting transcriptional activator protein mediates calcitriol action in the regulation of the expression of target genes. Cloning the vitamin D receptor gene (2,3) showed it to be a member of the ligand-activated receptor superfamily that includes the receptors for steroid hormones (glucocorticoids, progesterone, estrogen, androgen, and mineralocorticoids) as well as thyroid hormones and vitamin A derivatives (4,5), natural regulators of a large number of physiological and developmental processes. The mechanisms by which these receptor proteins mediate the regulation of gene expression has been a subject of intense research. Rare overt mutations have been identified that compromise the function of receptors and that cause major functional disorders in humans and animals. For example, mutations in the vitamin D receptor gene, resulting in vitamin D-resistant rickets (6), and in the androgen receptor, resulting in androgen insensitivity (7), have been reported, and in the estrogen receptor gene an infrequent natural polymorphism has been correlated with a high rate of spontaneous abortion (8). However, despite a wealth of molecular information, little is known of the potential contribution of natural allelic variation in receptor genes to diversity of response to steroidal hormones in normal physiology and in disease states.

Osteoporosis is a major public health problem among the elderly in most Western countries involving both enormous health care costs and debilitating long-term effects (Riggs NEJM). Since therapy of established osteoporosis remains far from satisfactory, prevention is the best choice. Preventative strategies for osteoporosis must focus upon development of peak bone density in early adulthood and minimisation of age-related and postmenopausal bone loss. Evidence from twin and family studies have shown strong genetic effects on peak bone density that is modifiable by hormonal factors, nutrition and life style (Kelly et al, OI).

Twin studies have demonstrated that monozygotic twin pairs have a much greater concordance for axial and appendicular bone density than do dizygotic pairs. Analysis of these data indicated that these genetic factors account for approximately 75% of the total variation on bone density. This effect has been confirmed in mother-daughter pair studies. The present inventors analysed the potential mechanisms of this genetic effect in the twin model. The present inventors found that the genetic effect was apparent in certain biochemical indices of bone turnover, such as osteocalcin, a marker of bone formation. Moreover amongst dizygotic twins the higher osteocalcin level was associated with the lower bone density. The present inventors have also found that the genetic effect can be shown with equal strength in another marker of bone formation, i.e., procollagen type I C-terminal propeptide and less strongly in a marker of bone breakdown, collagen type I C-terminal telopeptide. Under normal circumstances bone formation and bone breakdown are tightly linked or "coupled" in the twin physiological process of bone turnover. Thus the somewhat surprising results from the twin studies indicate that the bone formation markers, as markers of bone turnover, predict bone density and that genetic regulation of bone turnover is the pathway of the strong genetic effect on bone density.

The cross-sectional data on bone density in twins suggested that a single gene or set of genes is responsible for the genetic effect on bone density. However, it was unknown how this effect is mediated and which gene or genes influence bone density. In recent studies, using restriction fragment length polymorphism, the present inventors have shown common allelic variation in the vitamin D receptor (VDR) locus predict osteocalcin, independent of age, sex or menopausal status (Morrison et al, PNAS). The vitamin D receptor gene, as the active hormonal form of vitamin D (1,25-dihydroxyvitamin D) is an important central regulator of bone and calcium homeostasis modulating intestinal calcium absorption, bone formation, recruitment of the bone resorbing cell (osteoclast) and bone resorption per se as well as parathyroid hormone production and vitamin D's own activation in the kidney. Because of the likelihood that any alterations in the receptor for the active hormonal form of vitamin D could have such wide effects, the effect of these common VDR gene alleles on bone density was examined using a twin model. In the twin model, within-pair comparisons eliminate age and various cohort effects as confounders.

The studies have shown that common allelic variants in the VDR gene predict differences in bone density and account for 50–75% of the total genetic determination of bone density in the spine and hip.

It is believed that this a clear example that genotypic variations in transcriptional regulators of genes encoding regulatory and/or structural proteins, determine physiological set-points and predisposition to pathophysiological states with implications for susceptibility to disease and for determining likely responses to therapy.

Accordingly in a first aspect the present invention consists in a method of assessing in an individual's predisposition to a pathophysiological state and/or likely response to therapy comprising analysing genotypic variations in transcriptional regulators of genes encoding regulatory and/or structural proteins.

In a second aspect the present invention consists in a method of predicting predisposition of an individual to low or high bone density comprising analysing allelic variation within the vitamin D receptor gene of the individual.

in a preferred embodiment of the present invention the analysis comprises restriction fragment length polymorphism using endonuclease digestion.

In a further preferred embodiment of the present invention a segment of the vitamin D receptor is amplified using polymerase chain reaction prior to endonuclease digestion.

In yet a further preferred embodiment of the present invention the endonuclease is selected from the group consisting of Bsm1, Apa1, EcoRv and Taq1, and is most preferably Bsm1.

In another preferred embodiment of the present invention the segment of the vitamin D receptor is amplified using a pair of primers selected from the group consisting of

5'-CAACCAAGACTACAAGTACCGCGTCAGTGA-3' (SEQ ID:NO2)

and 5'-AACCAGCGGAAGAGGTCAAGGG-3'λ (SEQ ID:NO3);

and 5'-CAGAGCATGGACAGGGAGCAAG-3' (SEQ ID:NO4)

and 5'-GCAACTCCTCATGGCTGAGGTCTCA-3' λ (SEQ ID:NO5).

In a second aspect the present invention consists in a primer pair derived from the sequence of the VDR gene shown in Table 5 for use in amplifying a segment of the VDR gene using polymerase chain reaction, the segment including at least one of the Bsm1, Apa1 or Taq1 cut sites as shown in Table 5.

In a preferred embodiment of this aspect of the present invention the primer pair is 5'-CAACCAAGACTACAAGTACCGCGTCAGTGA-3' and 5'-AACCAGCGGAAGAGGTCAAGGG-3', or 5'-CAGAGCATGGACAGGGAGCAAG-3' and

5'-GCAACTCCTCATGGCTGAGGTCTCA-3'.

The allelic makeup of other transacting factors which may be assessed include oestrogen and androgen receptors to determine risk of osteoporosis and/or ischaemic heart disease. The allelic makeup of the androgen receptor may be also used to assess risk and responsiveness to therapeutic intervention in skin diseases. The allelic makeup of the glucocorticoid receptor and the retinoic acid receptor can be determined to assess risk of osteoporosis. The allelic makeup of the mineralocorticoid receptor can be determined to assess risk of hypertension and the allelic makeup of proto-oncogenes can be determined to assess cancer risk. Tissue specific regulators can also be assessed to determine osteoporosis/cancer risk.

In order that the nature of the present invention may be more clearly understood, preferred forms thereof will now be described with reference to the following examples and figures in which:

FIG. 1 shows lumbar BMD differences in twin pairs according to vitamin D receptor alleles.

FIG. 2 shows a map of the vitamin D receptor gene from exon 7 to the start of the 3' non-coding sequence of exon 9 showing the location of polymorphic restriction enzyme sites used in this study and the fragments amplified by PCR used to detect the RFLPs. Asterisk denotes polymorphic site while absence of the asterisk indicates an invariant site.

Figure 1:
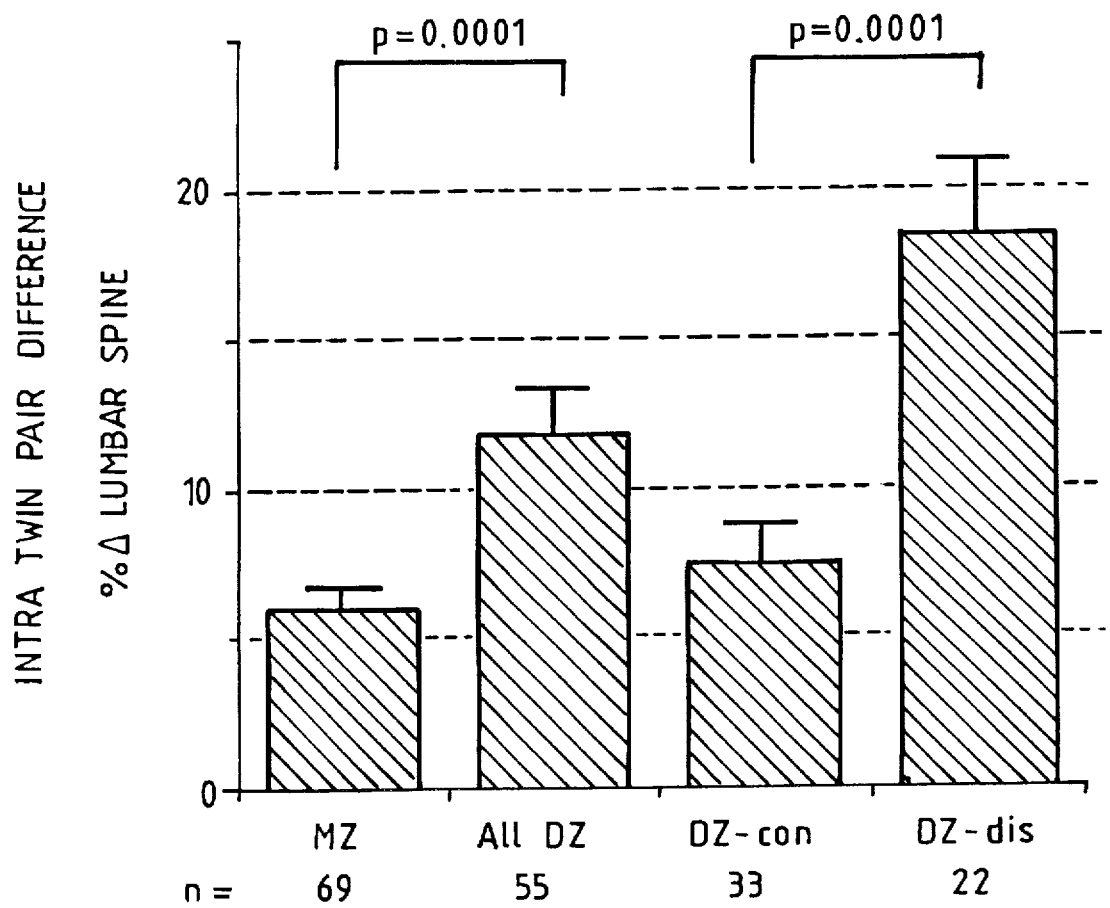

FIG. 7 shows bone density differences between twin pairs with respect to zygosity and concordance for VDR alleles. Bone density in the lumbar spine and proximal femur is expressed at the within pair percent difference in bone density in MZ and DZ twin pairs and according to whether the DZ twin pairs are concordant or discordant for the VDR. The DZ twins concordant for the VDR alleles are not significantly different from the MZ twins at any site, while the discordant DZ twins are significantly different (ANOVA) from both of these groups at each site. The difference between the total DZ group and those concordant for the VDR alleles compared with the MZ twins indicates that 75%; 48%, 59% and 90% of the genetic effect can be explained by the VDR alleles at the lumbar spine, femoral neck, Ward's triangle and trochanteric region of the proximal femur respectively. Genotype for another developmental transcriptional activator, retinoic acid receptor-α (21q7), did not predict ΔBMD at any site.

FIG. 8 shows the difference in bone density between dizygotic twin pairs with respect to degree of discordance for VDR. The difference in bone density between twin pairs is plotted in three groups; 0-complete concordance, 1-one allele different, 2-both alleles different. Panels A, B, C and D show the analyses for the VDR gene in the lumbar spine femoral neck, Ward's triangle and trochanteric region respectively. Regression analysis of this effect shows significant relationships at the lumbar spine (p=0.0001), Ward's triangle (p=0.006) and trochanteric region (p=0.034) and borderline at the femoral neck (p=0.055). Using the sib-pair variance approach, significant relationships were observed between the squared difference in bone density within each twin pair ($\Delta^2$) and concordance for the VDR gene alleles at the lumbar spine, femoral neck and Ward's triangle and borderline at the trochanteric region of the proximal femur.

| | |
|---|---|
| Lumbar spine $\Delta^2$ = | 0.015 + 0.038 * Degree of discordance (r = 0.43, p = 0.001) |
| Femoral neck $\Delta^2$ = | 0.015 + 0.016 * Degree of discordance (r = 0.29, p = 0.034) |
| Ward's triangle $\Delta^2$ = | 0.017 + 0.026 * Degree of discordance (r = 0.34, p = 0.01) |
| Trochanteric region $\Delta^2$ = | 0.015 + 0.015 * Degree of discordance (r = 0.27, p = 0.05) |

FIG. 9 shows higher bone mineral density associated with the b allele of the VDR gene.

A. Lumbar spine bone mineral densities of dizygotic twin pairs discordant for Bsm-1 alleles (n=22) are plotted as twin and co-twin according to genotype. Lines connect bone mineral density values for a twin pair. In 21 of 22 pairs, the twin carrying extra presence of the site (b) alleles has the higher bone mass (open circles). A single twin pair (black circles) has the reverse situation.

B. Bone mineral density at the lumbar spine amongst unrelated premenopausal females according to VDR genotype. One of each (premenopausal female) MZ and DZ twin pair was randomly selected for this analysis and the numbers of individuals are shown for each group. It is clear that the BB genotype has a lower mean BMD at the lumbar spine while the bb group has the higher mean BMD. The magnitude of this effect can be appreciated in relation to the standard deviation of bone density in an age-matched population of about 0.11 gm/cm² at each site. The mean ±SE is plotted and significance of the difference between groups was calculated by ANOVA. The pair-wise comparisons were made by unpaired Student's-tests. the different groups were not significantly different for age, height or weight.

Figure 10A:
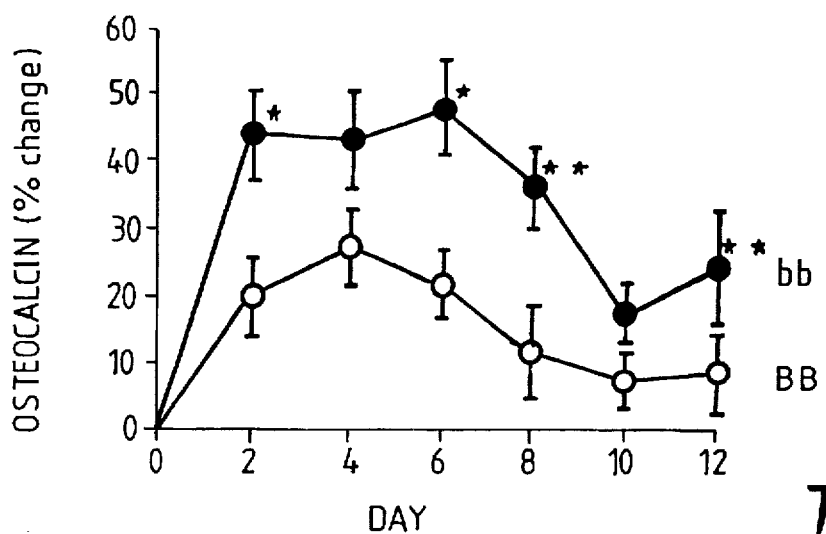
Figure 10B:
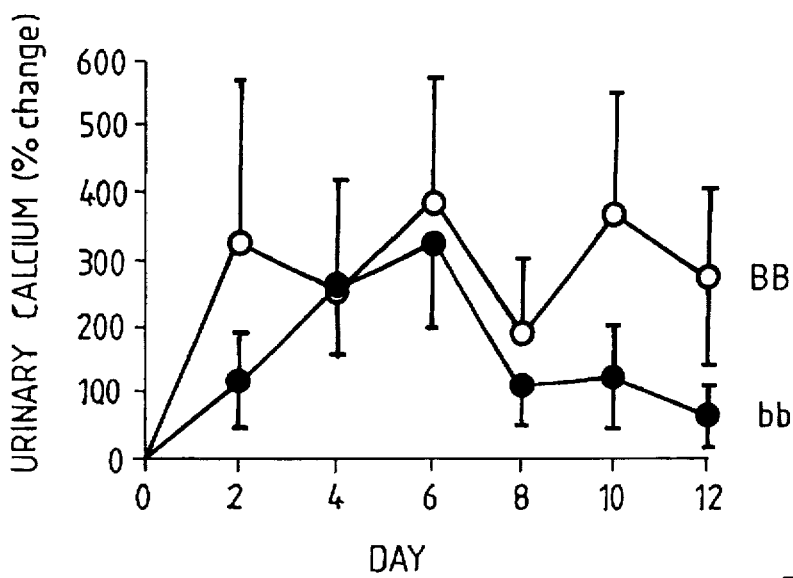
Figure 10C:
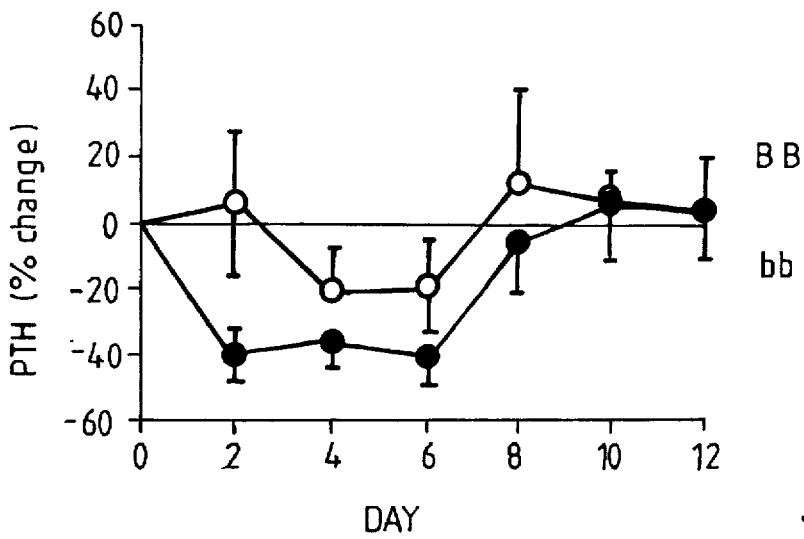

FIG. 10 shows the results of calcitriol therapy in individuals of different genotype.

STUDY 1

Methods

Two hundred eighty-eight subjects recruited for epidemiological studies of bone density were included in the study. All subjects were recruited from the Sydney metropolitan area, latitude 33°52'S, a region of high sunlight incidence. Ninety-one subjects of Caucasian British-Australian origin (United Kingdom and Irish background) with restriction fragment length polymorphism (RFLP) data for the three endonucleases had serum osteocalcin data available. None of the subjects was taking medication known to cause bone disease or influence osteocalcin levels. All subjects were Caucasian and had normal renal function as determined by serum creatinine.

Serum was collected in the morning after overnight fast, and none of the subjects was treated with calcitriol prior to venipuncture. Serum osteocalcin was determined by an in-house radioimmunoassay based on rabbit anti ovine osteocalcin (11). The normal range of osteocalcin found with this assay is 3–18 ng/ml when purified ovine osteocalcin is used. Osteocalcin determinations were made prior to, and independently of, the RFLP analysis and the results were stored in a coded fashion.

DNA Analysis. The probe used to identify RFLPs was a 2.1-kilobase-pair fragment of the vitamin D receptor cDNA (3,18) covering the entire coding region but lacking the 3' untranslated portion of the mRNA. Extraction of DNA from blood and Southern blotting were done by standard methods. Restriction enzymes were obtained from Pharmacia-LKB and New England Biolabs and used according to the suppliers' specifications.

Statistical Methods. The relative association of the RFLP markers was assessed statistically for deviation from the null hypothesis of free association by using contingency tables and $X^2$ tests. The Statview-plus-graphics statistical package (Abacus Concepts, Berkeley, Calif.) run on a Macintosh SE/30 computer was used for analysis of variance (ANOVA). Fisher's protected least-significant-difference (PLSD) test was used to assess the relationship between RFLP and serum osteocalcin. Significance levels quoted are for the initial F tests on the null hypothesis (no difference between the means) of the overall effect and for the confidence level of the pairwise comparison of the continuous variable means of each categorical (RFLP) class.

Each RFLP marker system was considered separately for its association with osteocalcin serum concentrations by ANOVA comparing categorical classes (RLFPs) against the continuous variable (osteocalcin). The osteocalcin values (ng/ml) were not normally distributed, and so nonparametric analysis was performed as well as logarithmic transformation as ln(1+osteocalcin).

Results

Two previously unreported frequent RFLPs (detected by Bsm I and EcoRV) were found by using the vitamin D receptor cDNA probe, in addition to a previously reported RFLP detected by Apa I (18). The RFLPs were coded as Aa (Apa I), Bb (Bsm I) and Ee (EcoRV), where the uppercase letter signifies absence of the site and lowercase signifies presence of the site. The Mendelian nature of the RFLPs was verified by family studies (data not shown). The frequencies of these RFLPs in 266 unselected volunteers unrelated to this study are shown in Table 1. The genotypes of 182 individuals were assessed with all three RFLPs (Table 2). They demonstrated a strong degree of coassociation, indicating linkage disequilibrium at this locus. The RFLPs were highly associated such that AA was found with BB and EE at frequencies of 83% and 92%, respectively; correspondingly, aa was found with bb and ee at frequencies of 61% and 72%, respectively. The subsequent functional analysis does not depend on haplotyping; however, only two of a possible eight haplotypes are needed to account for 53.2% of the test population. The apparent homozygotes define the most frequent possible haplotypes as a b e and A B E (Table 2).

TABLE 1

| | Frequencies of RFLP Alleles | | |
|---|---|---|---|
| Enzyme | Allele 1 | Allele 2 | n* |
| Apa I | A, 0.494 | a, 0.506 | 256 |
| Bsm I | B, 0.439 | b, 0.560 | 182 |
| EcoRV | E, 0.490 | e, 0.510 | 255 |

*No of individuals tested.

TABLE 2

| Frequencies of RFLP Genotypes | | | |
|---|---|---|---|
| Homozygotes | n* | Heterozygotes | n* |
| aa bb ee | 26 | Aa Bb Ee | 72 |
| AA BB EE | 19 | AA Bb EE | 13 |
| AA bb EE | 2 | aa Bb ee | 8 |
| aa BB ee | 2 | Aa Bb ee | 8 |
| | | Aa bb Ee | 7 |
| | | Aa bb ee | 4 |

*No. of individuals per 182 tested with all three RFLPs (heterozygote classes with <4 individuals have been excluded).

TABLE 3

| | Osteocalcin Values and Vitamin D Receptor Alleles | | | | | | |
|---|---|---|---|---|---|---|---|
| RFLP | n | Median | Mean | SD | SE | Sig. 1 | Sig. 2 | P value |
| Bsm I | | | | | | | | |
| BB | 16 | 16.8 | 2.86 | 0.45 | 0.11 | BBvsbb | BBvsBb | 0.0001 |
| Bb | 46 | 8.9 | 2.12 | 0.58 | 0.09 | 0.00005 | 0.0001 | |
| bb | 25 | 8.8 | 1.97 | 0.71 | 0.14 | | | |
| Total n | 87 | | | | | | | |

TABLE 3-continued

| RFLP | n | Median | Mean | SD | SE | Sig. 1 | Sig. 2 | P value |
|---|---|---|---|---|---|---|---|---|
| Apa 1 | | | | | | | | |
| AA | 25 | 14.0 | 2.53 | 0.63 | 0.13 | AAvsaa | AAvsAa | 0.0023 |
| Aa | 45 | 9.3 | 2.18 | 0.59 | 0.09 | 0.001 | 0.04 | |
| aa | 20 | 7.5 | 1.83 | 0.78 | 0.18 | | | |
| Total n | 90 | | | | | | | |
| EcoRV | | | | | | | | |
| EE | 26 | 14.0 | 2.53 | 0.63 | 0.12 | EEvsee | EEvsEe | 0.0153 |
| Ee | 45 | 8.8 | 2.11 | 0.60 | 0.09 | 0.015 | 0.015 | |
| ee | 18 | 10.5 | 2.02 | 0.83 | 0.20 | | | |
| Total n | 89 | | | | | | | |

Osteocalcin values among 91 Caucasian subjects of British-Australian origin (United Kingdom and Irish background) were analyzed with respect to the three informative RFLPs. As the osteocalcin values were not normally distributed, they were logarithmically transformed prior to statistical analysis. Median, median of serum osteocalcin values; Mean, mean of log-transformed values [ln (osteocalcin + 1)]; n, number of subjects; SD, standard deviation; Se, standard error of the mean; Sig., significance (probability that such a difference could occur by chance) referring to the difference between the means of the homozygotes (Sig. 1) and to the difference between the homozygote (absence of RFLP site) and the heterozygote (Sig. 2). P value is for the F test on the overall effect.

TABLE 4

Distribution of Subjects with respect to Age, Sex, and Menopausal Status with respect to RFLPs

| | Bsm I | | | Apa I | | | EcoRV | | |
|---|---|---|---|---|---|---|---|---|---|
| | BB | Bb | bb | AA | Aa | aa | EE | Ee | ee |
| No. of subjects | 16 | 46 | 25 | 25 | 45 | 20 | 26 | 45 | 18 |
| Age, years | 52 ± 14 | 50 ± 14 | 44 ± 14 | 51 ± 15 | 50 ± 15 | 45 ± 12 | 49 ± 14 | 50 ± 15 | 46 ± 12 |
| No. female | 16 | 38 | 20 | 22 | 36 | 18 | 23 | 38 | 15 |
| Post-menopausal | 10 | 18 | 7 | 13 | 17 | 6 | 10 | 22 | 7 |
| Pre-menopausal | 6 | 20 | 13 | 9 | 19 | 12 | 13 | 16 | 8 |
| No. male | 0 | 8 | 5 | 3 | 9 | 2 | 3 | 7 | 3 |

The relationship between RFLPs and serum osteocalcin was analyzed in the 91 normal subjects with serum osteocalcin data (Table 3). The distribution of this population with respect to age, sex, and menopausal status is shown in Table 4. Age was not significantly related to any RFLP genotype. The osteocalcin levels of the Bsm I BB group are significantly higher than those of the Bsm I bb group (P=0.0001). The other RFLPs show the same effect with highly significant P values for the Apa I allele system (AA versus aa, P<0.0025) and a weaker P value for the EcoRV RFLP (EE versus ee, P=0.015). With all three RFLPs the absence of restriction-site alleles (A, B, E) is associated with high osteocalcin levels and the presence of restriction-site alleles (b, a, and e, respectively) with low osteocalcin levels: BB, 16.8 ng/ml; Bb, 8.9 ng/ml; and bb, 8.8 ng/ml (medians). Nonparametric statistical analysis (Kruskal-Wallis) of raw osteocalcin values gave essentially the same results as ANOVA: Apa I, P-0.0016; Bsm I, P=0.0001; EcoRV, P=0.0044.

Figure 2:
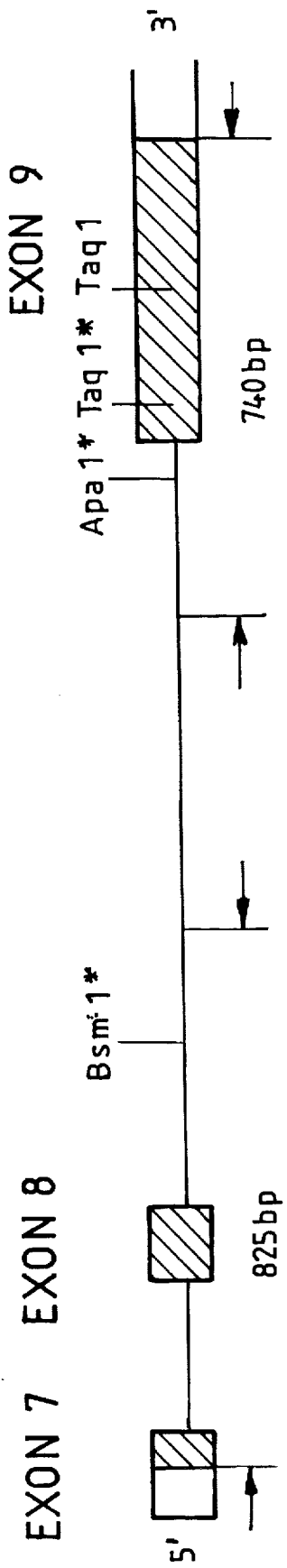

Since the Bsm I and Apa I RFLPs were the most predictive, the population was subdivided according to the nine possible combinations of these alleles. This produced a clear separation of the serum osteocalcin values according to genotype (FIG. 1). Since the weaker association of the EcoRV marker may be determined by its disequilibrium with the other markers, we examined the distribution of Apa I and Bsm I alleles and osteocalcin values within individuals with the EE genotype (FIG. 2). The Bsm I marker essentially dictated the inferred haplotypes and their associated osteocalcin values (P=0.003).

The genotype prediction of serum osteocalcin levels was maintained for Bsm I and Apa I when males (n=14) were excluded (Bsm I, P=0.0001; Apa I, P=0.0034; ANOVA values for the overall effect). Menopause has been associated with an increase in osteocalcin values, with a wide variation in osteocalcin values being observed in the early postmenopausal years (19–21). Therefore the role of menopausal status was assessed by multiple regression analysis and analysis of covariance including age, menopausal status, and Bsm I genotype. Menopausal status was a weaker determinant of serum osteocalcin concentrations than Bsm I polymorphism (r=−0.44, P<0.001). Two-factor ANOVA yielded the same result; Bsm I, P=0.0002; menopausal status, P=0.24. Analyzing premenopausal and postmenopausal women separately did not alter the results, and genotype was a stronger predictor than menopausal status (FIG. 1).

STUDY 2

Materials and Methods

Subjects

Subjects were 535 unrelated volunteers (447 females and 88 males) who had enrolled in studies of the effect of genetics on bone density. The subjects were obtained from requests through the media in the Sydney metropolitan area. The mean ages of the subjects were 51.4±13.8 yr (mean±SD; range 20–84 yr) for females and 40.6±16.0 yr (20–79 yr) for males. Subjects in this analysis were of Caucasian British-Australian origin (United Kingdom and Irish background). Menopausal status was confirmed by the presence of elevated FSH and LH and low estradiol levels, with an absence of menses for at least 12 months. Subjects with a history of bone disease, illness, bilateral ovarectomy or drug use (including hormone replacement therapy) which could affect bone turnover and bone density were excluded from this study.

Bone Mineral Density Analysis

Bone mineral density (BMD), expressed as an area density in g/cm², was measured in the lumbar spine (L2-4) and femoral neck using either dual photon absorptiometry or dual energy x-ray absorptiometry (Lunar DP3 or DEXA, respectively, Lunar Radiation NCo. Madison, Wis.) as previously described (Pocock et al. 1987).

DNA Analysis; PCR (Polymerase chain Reaction) and RFLP Analysis using Endonuclease Digestion Blood was collected into heparin treated tubes and leukocytes separated by sedimentation trough physiological saline solution in a clinical centrifuge. Purified leukocytes were lysed in leukocyte lysis buffer (10 mM Tris-HCl, pH7.4, physiological saline and 0.5% w/v sodium dodecyl sulphate). Lysate was treated with proteinase K (Applied Biosciences, Palo Alto U.S.A.) at 50 ug/ml for 2 hour at 65 Celsius. DNA was extracted by repetitive phenol chloroform solvent extraction as described in Maniatis et al. and ethanol precipitated prior. DNA was redissolved in TE buffer (10 mM Tris-HCl, 1 mM EDTA, pH 8.0) and quantitated by ultraviolet absorbance at 260 Nm.

The vitamin D receptor gene from exon 7 to the 3'-untranslated region was sequenced. The sequence is set out in Table 5, (SEQ ID:NO1).

Four oligonucleotide primers were synthesized to amplify the 3' flanking region of the VDR gene. Detection of the Bsm1 site was facilitated by amplifying a region spanning the site, with one primer originating in exon 7(5'-CAAC-CAAGACTACAAGTACCGCGTCAGTGA-3') and the other in intron 8(5'-AACCAGCGGAAGAGGTCAAGGG-3') producing a 825 base pair fragment. Detection of ApaI and TaqI sites was facilitated using a single amplification one

TABLE 5

(SEQ ID NO: 1)

Sequence Range: 1 to 2169

```
         10        20        30        40        50
         *         *         *         *         *
CAACC AAGAC TACAA GTACC GCGTC AGTGA CGTGA CCAAA GGTAT GCCTA GACTC
GTTGG TTCTG ATGTT CATGG CGCAG TCACT GCACT GGTTT CCATA CGGAT CTGAG
                            primer 490   Exon 7   |   Intron 7

60        70        80        90       100       110
         *         *         *         *         *         *
CACCT CCTGG GGAGT CTTTT TCAGC TCCCA GATTC TGGCT CCACC CGTCC TGGGG
GTGGA GGACC CCTCA GAAAA AGTCG AGGGT CTAAG ACCGA GGTGG GCAGG ACCCC 120       130       140       150       160
         *         *         *         *         *
TTTGG CTCCA ATCAG ATACA TGGGA GGGAG TTAGG CACCA ACAGG GAGAG AAGGG
AAACC GAGGT TAGTC TATGT ACCCT CCCTC AATCC GTGGT TGTCC CTCTC TTCCC 170       180       190       200       210       220
         *         *         *         *         *         *
CGAGG GTCAG ACCCA TGGGG TTGGA GGTGG GTGGG CGGCT CCTCA GCTCT TGCCC
GCTCC CAGTC TGGGT ACCCC AACCT CCACC CACCC GCCGA GGAGT CGAGA ACGGG 230       240       250       260       270
         *         *         *         *         *
GCAGT ACCTG GCCAT TGTCT CTCAC AGGCC GGACA CAGCC TGGAG CTGAT TGAGC
CGTCA TGGAC CGGTA ACAGA GAGTG TCCGG CCTGT GTCGG ACCTC GACTA ACTCG
             Intron 7            |    Exon 8    primer 757

280       290       300       310       320       330
         *         *         *         *         *         *
CCCTC ATCAA GTTCC AGGTG GGACT GAAGA AGCTG AACTT GCATG AGGAG GAGCA
GGGAG TAGTT CAAGG TCCAC CCTGA CTTCT TCGAC TTGAA CGTAC TCCTC CTCGT
            primer 758                                primer 456

340       350       360       370       380
         *         *         *         *         *
TGTCC TGCTC ATGGC CATCT GCATC GTCTC CCCAG GTATG GGGCC AGGCA GGGAG
ACAGG ACGAG TACCG GTAGA CGTAG CAGAG GGGTC CATAC CCCGG TCCGT CCCTC
                                   Exon 8   |  Intron 8

>Sac1
      |
      390       400       410       420       430       440
       *         *         *         *         *         *
GAGCT CAGGG ACCTG GGGAG CGGGG AGTAT GAAGG ACAAA GACCT GCTGA GGGCC
CTCGA GTCCC TGGAC CCCTC GCCCC TCATA CTTCC TGTTT CTGGA CGACT CCCGG 450       450       470       480       490
         *         *         *         *         *
AGCTG GGCAA CCTGA AGGGA GACGT AGCAA AAGGA GACAC AGATA AGGAA ATACC
TCGAC CCGTT GGACT TCCCT CTGCA TCGTT TTCCT CTGTG TCTAT TCCTT TATGG
```

TABLE 5-continued (SEQ ID NO: 1)

```
       500         510         520         530         540         550
        *           *           *           *           *           *
   TACTT TGCTG GTTTG CAGAG CCCCT GTGGT GTGTG GACGC TGAGG TGCCC CTCAC
   ATGAA ACGAC CAAAC GTCTC GGGGA CACCA CACAC CTGCG ACTCC ACGGG GAGTG 560         570         580         590         600
              *           *           *           *           *
      TGCCC TTAGC TCTGC CTTGC AGAGT GTGCA GGCGA TTCGG TAGGG GGGAT TCTGA
      ACGGG AATCG AGACG GAACG TCTCA CACGT CCGCT AAGCC ATCCC CCCTA AGACT
        primer 834

Polymorphic site      >BsmI
                                                                |
       610         620         630         640         650         660
        *           *           *           *           | *         *
   GGAAC TAGAT AAGCA GGGTT CCTGG GGCCA CAGAC AGGCC TGCGC ATTCC CAATA
   CCTTG ATCTA TTCGT CCCAA GGACC CCGGT GTCTG TCCGG ACGCG TAAGG GTTAT 670         680         690         700         710
              *           *           *           *           *
   CTCAG GCTCT GCTCT TGCGT GAACT GGGCT CAACA TTCCT GTTAT TTGAG GTTTC
   GAGTC CGAGA CGAGA ACGCA CTTGA CCCGA GTTGT AAGGA CAATA AACTC CAAAG 720         730         740         740         760         770
        *           *           *           *           *           *
   TTGCG GGCAG GGTAC AAAAC TTTGG AGCCT GAGAG ATGGT TCTGC CTATA TAGTT
   AACGC CCGTC CCATG TTTTG AAACC TCGGA CTCTC TACCA AGACG GATAT ATCAA 780         790         800         810         820
              *           *           *           *           *
   TACCT GATTG ATTTT GGAGG CAATG TGCAG TGACC CTTGA CCTCT TCCGC TGGTT
   ATGGA CTAAC TAAAA CCTCC GTTAC ACGTC ACTGG GAACT GGAGA AGGCG ACCAA 830         840         850         860         870         880
        *           *           *           *           *           *
   AGAGG TGAGA AGAGG GAGAA AAGGC CGAAG AGAAG TTATT GTGAC CTTGG GACAT
   TCTCC ACTCT TCTCC CTCTT TTCCG GCTTC TCTTC AATAA CACTG GAACC CTGTA 890         900         910         920         930
              *           *           *           *           *
   GATGT CGGTG ATGAG GTCCA AAGAG GGGCG GCCCT GCCTC AGCCT GTGCT AGTGG
   CTACA GCCAC TACTC CAGGT TTCTC CCCGC CGGGA CGGAG TCGGA CACGA TCACC 940         950         960         970         980         990
        *           *           *           *           *           *
   CCTGT GCCCA GGGAT GCTTT CCTGG ACTGG AGGCT CAAGG AATGG AGATG GCTCC
   GGACA CGGGT CCCTA CGAAA GGACC TGACC TCCGA GTTCC TTACC TCTAC CGAGG 1000        1010        1020        1030        1040
              *           *           *           *           *
   TCTAC CCCTG CCCAG CCAGC CTTCT CTCAT TCATT CATCC ACTTA GCAAC AATTT
   AGATG GGGAC GGGTC GGTCG GAAGA GAGTA AGTAA GTAGG TGAAT CGTTG TTAAA >KpnI
      1050    | 1060        1070        1080        1090        1100
        *     |   *           *           *           *           *
   ATTGA GCACC TATTA GGTAC CAGGC ACTAT GCTAG GTACT GGGGT TCAGC AGCAA
   TAACT CGTGG ATAAT CCATG GTCCG TGATA CGATC CATGA CCCCA AGTCG TCGTT >Hind3
                                   |
      1110        1120        | 1130        1140        1150
        *           *         |   *           *           *
   ATGGG ACACA GGCTC CTCTC CCATG AAGCT TAGGA GGAAA CATTA AACAA ATGTT
   TACCC TGTGT CCGAG GAGAG GGTAC TTCGA ATCCT CCTTT GTAAT TTGTT TACAA >AseI                          >DraI
           |                              |
      1160 |    1170        1180       1190        1200        1210
        *  |      *           *        |  *           *           *
   ATTTA ATTAT TAATT CCTAA CAAGG CAAGA GTTTT AAAAA TAAAG TAAGT GATGC
   TAAAT TAATA ATTAA GGATT GTTCC GTTCT CAAAA TTTTT ATTTC ATTCA CTACG 1220        1230        1240        1250        1260
              *           *           *           *           *
   TACAG AAGGG TAGAA TAGAA GGAGG GAAGC TGACG TGGTC TGGGC TACAG AGGTA
   ATGTC TTCCC ATCTT ATCTT CCTCC CTTCG ACTGC ACCAG ACCCG ATGTC TCCAT
```

TABLE 5-continued (SEQ ID NO: 1)

```
                                                                    >Sau3A1
                                                                    |
     1270       1280       1290       1300       1310       1320
      *          *          *          *          *          *
   GAGTG TTGCC AGGAA TGGCC TTTTG GAGGA AGACC TTTTA AGCTG TTATC CAAAG
   CTCAC AACGG TCCTT ACCGG AAAAC CTCCT TCTGG AAAAT TCGAC AATAG GTTTC 1330       1340       1350       1360       1370
       *          *          *          *          *          *
   GATCA GTAAG AGTCT GGCAA AGATA GCAGA GCAGA GTTCC AAGCA GAGGG AGCAC
   CTAGT CATTC TCAGA CCGTT TCTAT CGTCT CGTCT CAAGG TTCGT CTCCC TCGTG 1380       1390       1400       1410       1420       1430
      *          *          *          *          *          *
   AGATG TGAAG GCTGG TGGCA GAGAG CATGG CGCAT CGGGT CGCTG AGGGA TGGAC
   TCTAC ACTTC CGACC ACCGT CTCTC GTACC GCGTA GCCCA GCGAC TCCCT ACCTG 1440       1450       1460       1470       1480
      *          *          *          *          *          *
   AGAGC ATGGA CAGGG AGCAA GGCCA GGCAG GGACA GGGCC AGGTG CGCCC ATGGA
   TCTCG TACCT GTCCC TCGTT CCGGT CCGTC CCTGT CCCGG TCCAC GCGGG TACCT

>Sau3A1
                |
                >BamH1
                |
     1490       1500       1510       1520       1530       1540
      *          *       | *          *          *          *          *
   AGGAC CTAGG TCTGG ATCCT AAATG CACGG AGAAG TCACT GGAGG GCTTT GGGGC
   TCCTG GATCC AGACC TAGGA TTTAC GTGCC TCTTC AGTGA CCTCC CGAAA CCCCG 1550       1560       1570       1580       1590
      *          *          *          *          *          *
   CAGGC AGTGG TATCA CCGGT CAGCA GTCAT AGAGG GGTGG CCTAG GGGGT GCTGC
   GTCCG TCACC ATAGT GGCCA GTCGT CAGTA TCTCC CCACC GGATC CCCCA CGACG

Polymorphic site  >Apa1
                                                                    |
     1600       1610       1620       1630       1640       | 1650
      *          *          *          *          *        * |       *
   CGTTG AGTGT CTGTG TGGGT GGGGG GTGGT GGGAT TGAGC AGTGA GGGGC CCAGC
   GCAAC TCACA GACAC ACCCA CCCCC CACCA CCCTA ACTCG TCACT CCCCG GGTCG >Sac1                            >Sau3A1
                |                                |
     *        | 1660       1670       1680      | 1690       1700
              |  *          *          *        | *          *         *
   TGAGA GCTCC TGTGC CTTCT CTATC CCCGT GCCCA CAGAT CGTCC TGGGG TGCAG
   ACTCT CGAGG ACACG GAAGA GATAG GGGCA CGGGT GTCTA GCAGG ACCCC ACGTC
                                          Intron 8          |  Exon 9

Absence of Taq site
                   GATCGAGGCC = Taq1+ allele

>Pst1
                                                                 |
     1710       1720       1730       1740       1750       | 1760
      *          *          *          *          *        *  |       *
   GACGC CGCGC TGATT GAGGC CATCC AGGAC CGCCT GTCCA ACACA CTGCA GACGT
   CTGCG GCGCG ACTAA CTCCG GTAGG TCCTG GCGGA CAGGT TGTGT GACGT CTGCA
                      Primer 466                           primer 455 and >Sau3A1
                                                                    |
     1770       1780       1790       1800       1810       |
      *          *          *          *          *        *  |       *
   ACATC CGCTG CCGCC ACCCG CCCCC GGGCA GCCAC CTGCT CTATG CCAAG ATGAT
   TGTAG GCGAC GGCGG TGGGC GGGGG CCCGT CGGTG GACGA GATAC GGTTC TACTA
   770 (reverse 455)
```

TABLE 5-continued (SEQ ID NO: 1)

```
     1820       1830       1840       1850       1860       1870
      *          *          *          *          *          *
CCAGA AGCTA GCCGA CCTGC GCAGC CTCAA TGAGG AGCAC TCCAA GCAGT ACCGC
GGTCT TCGAT CGGCT GGACG CGTCG GAGTT ACTCC TCGTG AGGTT CGTCA TGGCG
primer 467

1880       1890       1900       1910       1920
      *          *          *          *          *
TGCCT CTCCT TCCAG CCTGA GTGCA GCATG AAGCT AACGC CCCTT GTGCT CGAAG
ACGGA GAGGA AGGTC GGACT CACGT CGTAC TTCGA TTGCG GGGAA CACGA GCTTC
                                      primer 468

>Sau3A1
           |
     1930  |    1940       1950       1960       1970       1980
      *    |     *          *          *          *          *
TGTTT GGCAA TGAGA TCTCC TGACT AGGAC AGCCT GTGCG GTGCC TGGGT GGGGC
ACAAA CCGTT ACTCT AGAGG ACTGA TCCTG TCGGA CACGC CACGG ACCCA CCCCG 1990       2000       2010       2020       2030
      *          *          *          *          *
TGCTC CTCCA GGGCC ACGTG CCAGG CCCGG GGCTG GCGGC TACTC AGCAG CCCTC
ACGAG GAGGT CCCGG TGCAC GGTCC GGGCC CCGAC CGCCG ATGAG TCGTC GGGAG
                                                    primer 459

2040       2050       2060       2070       2080       2090
      *          *          *          *          *          *
CTCAC CCGTC TGGGG TTCAG CCCCT CCTCT GCCAC CTCCC CTATC CACCC AGCCC
GAGTG GGCAG ACCCC AAGTC GGGGA GGAGA CGGTG GAGGG GATAG GTGGG TCGGG 2100       2110       2120       2130       2140
      *          *          *          *          *
ATTCT CTCTC CTGTC CAACC TAACC CCTTT CCTGC GGGCT TTTCC CCGGT CCCTT
TAAGA GAGAG GACAG GTTGG ATTGG GGAAA GGACG CCCGA AAAGG GGCCA GGGAA 2150       2160
      *          *
GAGAC CTCAG CCATG AGGAG TTGC
CTCTG GAGTC GGTAC TCCTC AACG
primer 465
```

Primer underlined on top strand is a foward primer, those on the bottom strand are reverse primers.
Any pair wise combination of these primers or primers based on this and surrounding sequence can amplify the region by polymerase chain reaction.

--- primer in intron 8(5'-CAGAGCATGGACAGGGAG-CAAG-3') and the other in exon 9 (5'-GCAACTCCTCATG-GCTGAGGTCTCA-3' producing a 740 base pair fragment (FIG. 2).

PCR was carried out in a volume of 20 ul containing 200ng genomic DNA, 20 pmol of each primer, 200 uM dNTPs, 50 mM KCl, 10mM Tris (pH8.3), 1.5 mM, MgCl$_2$ and 1 U Taq DNA polymerase (TOYOBO, Osaka, Japan). Each sample was subjected to 37 amplification cycles as follows: Step 1 –3 min at 94° C., 1 min at 62° C., 2 min at 72° C.; Step 2 to 6 –20 sec at 94° C., 20 sec at 62° C., 1 min at 72° C., Step 7 to 36 –5 sec, 5 sec, 30 sec respectively. Amplification regimes should be optimised for any particular thermal cycling device. A 10 ul aliquot of each PCR product was digested with 5 units of endonuclease Bsm1 at 65° C. (New England Biolabs, Massachusettes U.S.A.), Apa1 at 37° C. or Taq1* (Promega Co. Australia) at 65° C. for 1 hour. A clone of an unrelated gene was used as an internal control for both Bsm1 and Apa1 digestion. For Taq1 digestion, an invariant Taq1 site in the PCR product itself was used as an internal control. The digested PCR products were separated on 1.2% (Bsm1 and Apa1), or 2.0% (Taq1) agarose gels containing 0.5 ug/ml ethidium bromide, 0.09M Tris-Borate and 0.002M EDTA, pH 8.3 for 1 hr at 100 V. EcoRI digested SPP1 marker (Bresatec Limited, Adelaide, Australia) was used as the size standard for all agarose gels.

Due to the sequence of the relevant sites several other restriction enzymes can be used to detect these polymorphisms. Bsm1 site sequence from an invariant adjacent Stu-1 site; B allele AGGCCTGCGCATTCCC (SEQ ID:NO 6), b allele underlined G is an A. This sequence change can be detected with Aos1, Fsp1, Mst1, Fdi2, Hinp1, Hha1 and their isoschizomers. Sequence at the polymorphic Apa1 site ending in an adjacent invariant Pvu2 site is: A allele GAGG GGCCCAGCTG (SEQ ID:NO 7), in the a allele the underlined G is a T. The presence of the G can be detected by Ban2, Aoc2, Pss1, Pal1, Hae3, Cfr3I, Asul, Sau96I, Eco0109I, Dra2, and isoschizomers. The presence of the T creates a polymorphisms for Ban1, and its isoschizomers. The sequence of the Taq1 polymorphism spanning invariant Hba1 to Hae3 sites is: T allele GCGCTGATTGAGGCC (SEQ ID:NO 8), in the t allele the underlined T is a C. This polymorphism can be also detected by Mbo1, Sau3A, Dpn1 and their isoschizomers.

Taq1* RFLP: We have previously reported that Bsm1 and Apa1 RFLPs in the vitamin D receptor gene predict serum osteocalcin levels. These polymorphic sites are located in the region of genomic DNA from exon 7 to the 3' untranslated region (3'-UTR). To characterize the differences between two common vitamin D receptor gene alleles (AB and ab), we have sequenced this region in homozygotes of genotypes AABB, aabb. We have identified a number of sequence differences, including 15 non coding changes. There is a single synonymous coding region change, a T for C in an isoleucine codon (ATT to ATC, isoleucine codons) in exon 9.

Statistical Analysis

Analysis of the variance (ANOVA) was performed using Statview+Graphics statistical package (Abacus Concepts, Berkeley, Calif., U.S.A.) on a Macintosh SE/30 computer. Fisher's protected least-significant-difference (PLSD) test was used to assess the relationship between RFLP and the BMD, height, weight. Significance levels quoted are for the initial F tests on the null hypothesis (no difference between the means) of the overall effect and for the confidence level of the pairwise comparison of the continuous variable means of each categorical (RFLP) class. Students t-test was used for pairwise comparisons. Relationships of continuous and categorical variables were established by multiple regression. Relationships between RFLP markers were established by contingency tables and Chi square.

Results

The frequencies of these three RFLPs in 535 subjects are shown Table 6. The RFLPs were coded as Bb (Bsm1), Aa (Apa1) and Tt (Taq1), where the uppercase letter signifies absence of the site and lowercase signifies presence of the site. The frequencies of Bsm1 and Apa1 RFLP are similar to that set out above (Table 1). RFLPs had a high degree of coassociation (Table 7). The AA genotype is highly associated with BB and tt at frequencies 92.7% and 95.3%, respectively; correspondingly, aa was found with bb and TT at frequencies of 61.6% and 65.3%, respectively. Comparing Bsm1 with Taq1 RFLP, tt, Tt, and TT genotypes are highly associated with BB, Bb and bb at frequencies 95.5%, 95.1% and 96.4% respectively. Because the Bsm1 and Taq1 results are so closely correlated, in subsequent discussions we have equated Bsm1 and Taq1 results and will refer only to Bsm1 results.

Figure 3:
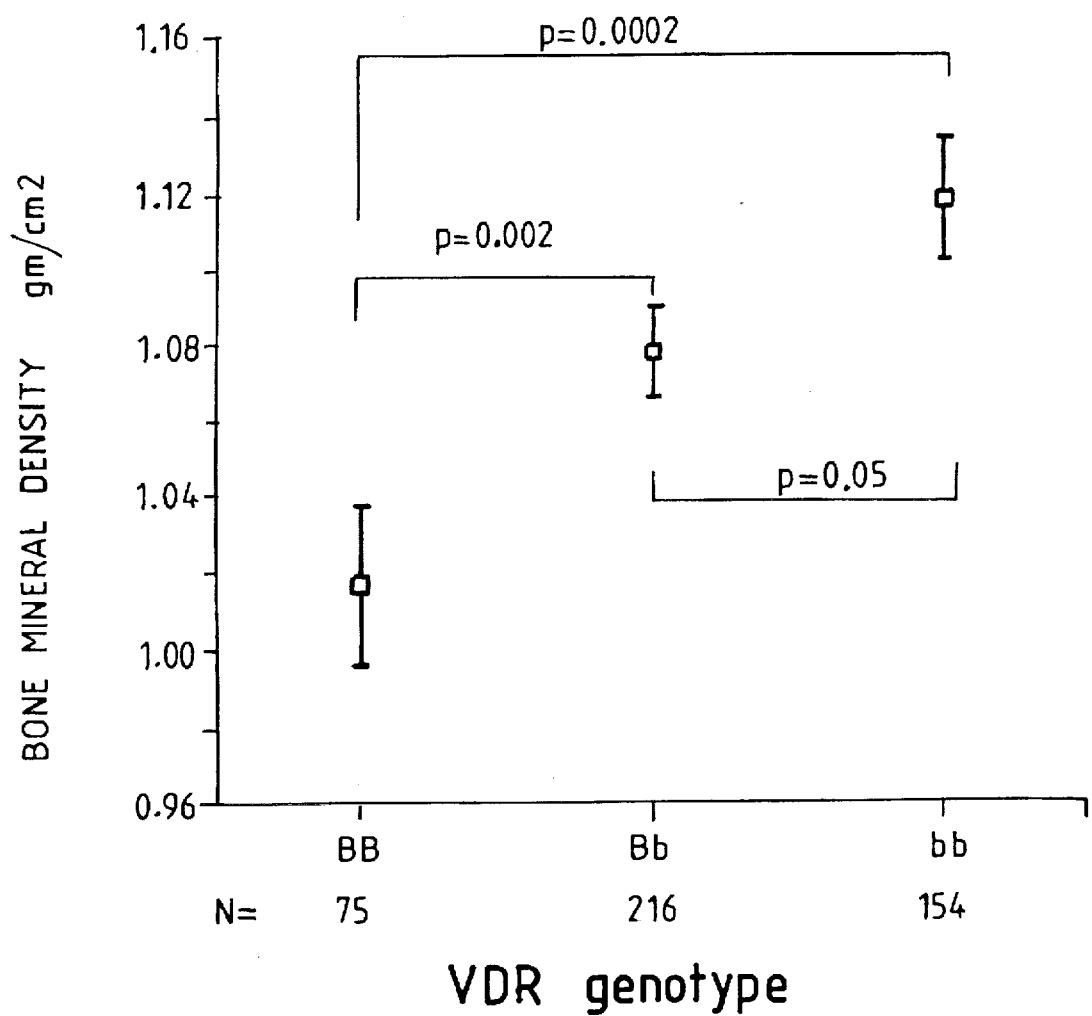
FIG. 3 shows bone mineral density is different in VDR genotypes: female subjects. Data shows the population mean±standard error mean. p values are for the pairwise two-sided Students t-tests for the groups.
Figure 4:
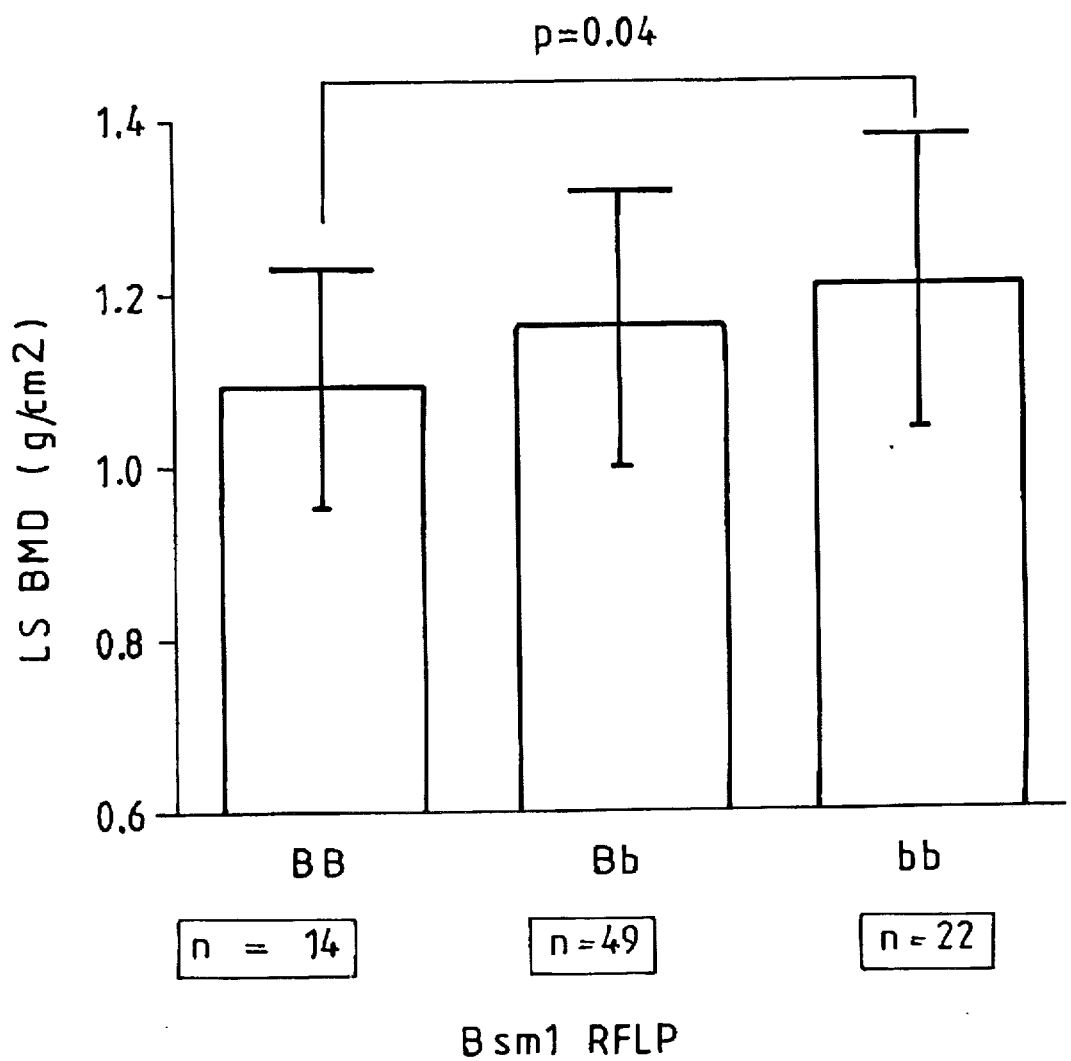
FIG. 4 shows the genetic effect on bone mass at the lumbar spine is also apparent in males. Symbols are as for FIG. 3.

The relationship between RFLPs and BMD at both LS and FN sites were analyzed in the 535 subjects. The distribution of this population with respect to age, height, weight, and menopausal status is shown in Table 8. Age, height, and weight were not significantly related to any RFLP genotype (Table 9). In females, mean LS BMD of the BB and AA group are 9.9% (1.017 vs 1.118) and 8.6% (1.049 vs 1.139) lower than those of the bb and aa groups respectively. The FN BMD of the BB and AA groups are also 5.6% and 5.3% lower than those of the bb and aa groups respectively. A heterozygote effect indicating co-dominance of alleles was also observed (FIG. 3). Lower LS and FN BMD were associated with the absence of both restriction site alleles (BA). The differences of mean BMD at LS and FN between BBAA genotype and bbaa genotype was wider

TABLE 6

Frequencies of RFLPs in study population.

| Genotype | N | Frequency % | Allele |
|---|---|---|---|
| BB | 89 | 16.8 | B = 0.418 |
| Bb | 266 | 50.1 | b = 0.582 |
| bb | 176 | 33.1 | |
| AA | 133 | 25.5 | A = 0.512 |
| Aa | 268 | 51.3 | a = 0.488 |
| aa | 121 | 23.2 | |
| TT | 188 | 35.4 | T = 0.596 |
| Tt | 257 | 48.4 | t = 0.404 |
| tt | 86 | 16.2 | |

TABLE 7

RFLP markers have a high degree of coassociation. Bsm-1 genotypes tabulated with Apa-1 and Taq1 genotypes. n refers to number of individuals. Chi square value and p value reflect the rejection of the null hypothesis of no association between the markers.

| Marker | BB | Bb | bb | total n |
|---|---|---|---|---|
| AA | 78 | 44 | 11 | 133 |
| Aa | 5 | 206 | 56 | 267 |
| aa | 4 | 8 | 106 | 118 |
| total n | 87 | 258 | 173 | 518 |

$Chi^2 = 428$
$p = 0.0001$

| | BB | Bb | bb | total n |
|---|---|---|---|---|
| TT | 1 | 14 | 173 | 188 |
| Tt | 5 | 249 | 3 | 257 |
| a | 83 | 3 | 0 | 86 |
| total n | 89 | 266 | 176 | 531 |

$Chi^2 = 912$
$p = 0.0001$

TABLE 8

Population characteristics of study group

| Sex | Number |
|---|---|
| Males | 88 |
| Females | 447 |
| Premenopausal | 185 |
| Postmenopausal | 262 |
| Mean years since menopause ± SEM | 11.3 ± 0.07 |

Mean values of anthropomorphic parameters in total subjects (±SEM).

| Age (year) | 49.6 + 0.6 |
|---|---|
| Height (cm) | 163.8 + 0.4 |
| Weight (kg) | 64.8 + 0.5 |

TABLE 9

Mean values of anthropomorphic parameters according to Bsm-1 genotype

| Genotype | n | Age | Height | Weight |
|---|---|---|---|---|
| Females | | | | |
| BB | 75 | 50 + 2 | 162 + 1 | 62 + 1 |
| Bb | 216 | 51 + 1 | 161 + 1 | 63 + 1 |
| bb | 154 | 52 + 1 | 161 + 1 | 64 + 1 |
| p value | | 0.6 | 0.3 | 0.9 |
| Males | | | | |
| BB | 14 | 35 + 4 | 177 + 2 | 72 + 10 |
| Bb | 50 | 41 + 2 | 176 + 1 | 75 + 10 |
| bb | 22 | 42 + 4 | 176 + 2 | 74 + 14 |
| p value | | 0.9 | 0.6 | 0.4 |

(13.4%, 7.8% respectively) than those of BB and bb or AA and aa (Table 9).

The effect of genotype was assessed by multiple regression analysis of covariance including age(yr), menopausal status (year post menopause; YPM), height (cm), weight (kg) and Bsm1 genotype (BB=1, Bb=2, bb=3) in females, giving the equation; LS BMD (g/cm2)=0.419+0.054 Bsm1 genotype −0.004 age −0.994 YPM+0.02 weight+0.004 height (n=425) r=0.58 R2=0.34,

|         | Bsm1   | age    | YPM    | Weight | Height |
|---------|--------|--------|--------|--------|--------|
| p value | 0.0001 | 0.0013 | 0.0001 | 0.0045 | 0.003  |
| F-score | 24.9   | 16.0   | 10.4   | 8.2    | 8.9    |

FN BMD g/cm2)=0.456+0.025 Bsm1 genotype −0.004 age −0.004 YPM+0.04 weight+0.02 height (n=425) 4=0.68, R2=0.47

|         | Bsm1  | age    | YPM    | Weight | Height |
|---------|-------|--------|--------|--------|--------|
| p value | 0.002 | 0.0001 | 0.0004 | 0.0001 | 0.022  |
| F-score | 9.6   | 41.7   | 12.8   | 35.2   | 5.3    |

Both lumbar spine and femoral neck BMD were negatively and independently correlated with-the menopausal status, age, Bsm1 RFP was also correlated independently with BMD at LS and F in females. Male's results were as follows:

LS BMD (g/cm2)=1.039+0.058 Bsm1 genotype (n=85)
r=0.22 RS=0.05, p=0.038, F-score 4.9
FN BMD(g/cm2)=1.046−0.003 age (n=85)
r=0./32, R2=0.10, p=0.017, F-score 5.9

Intercept with the Fracture Threshold

Figure 5B:
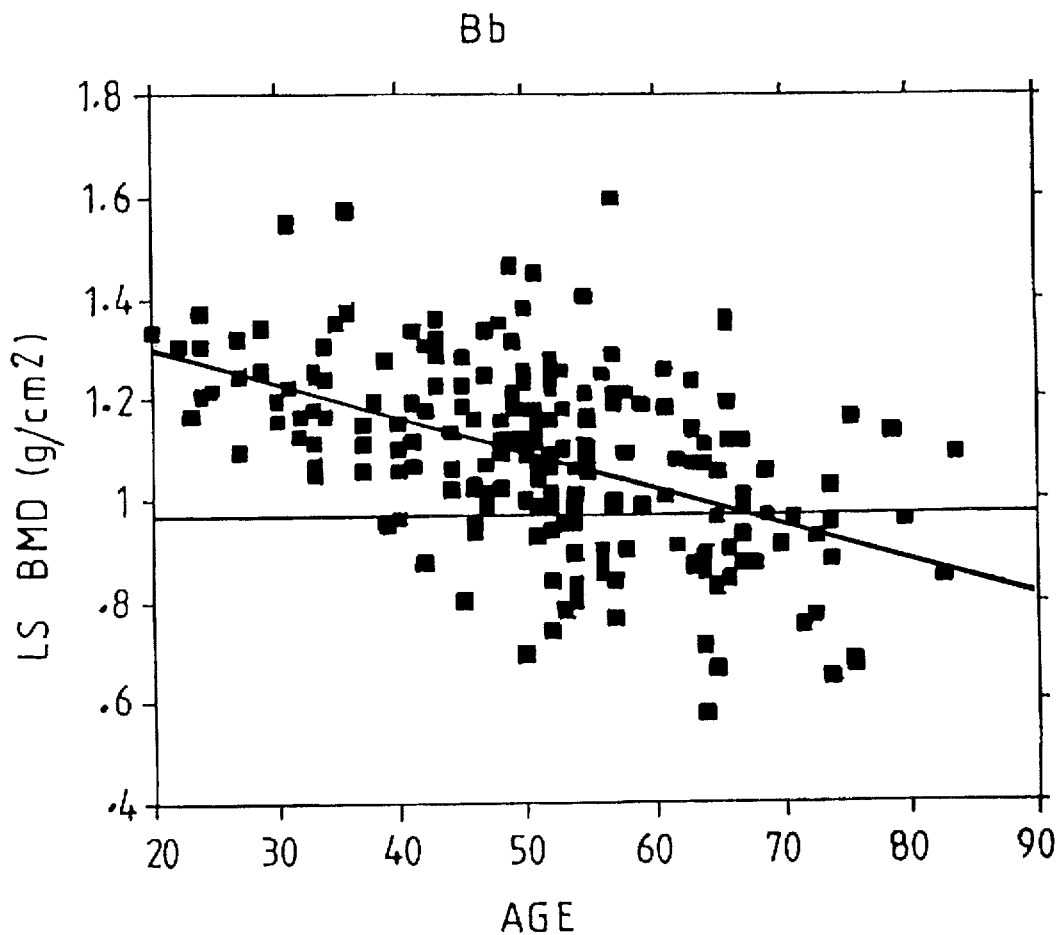
FIG. 5 shows age related regression of lumbar spine bone mineral density and intersection with the fracture threshold according to genotype.
Figure 5C:
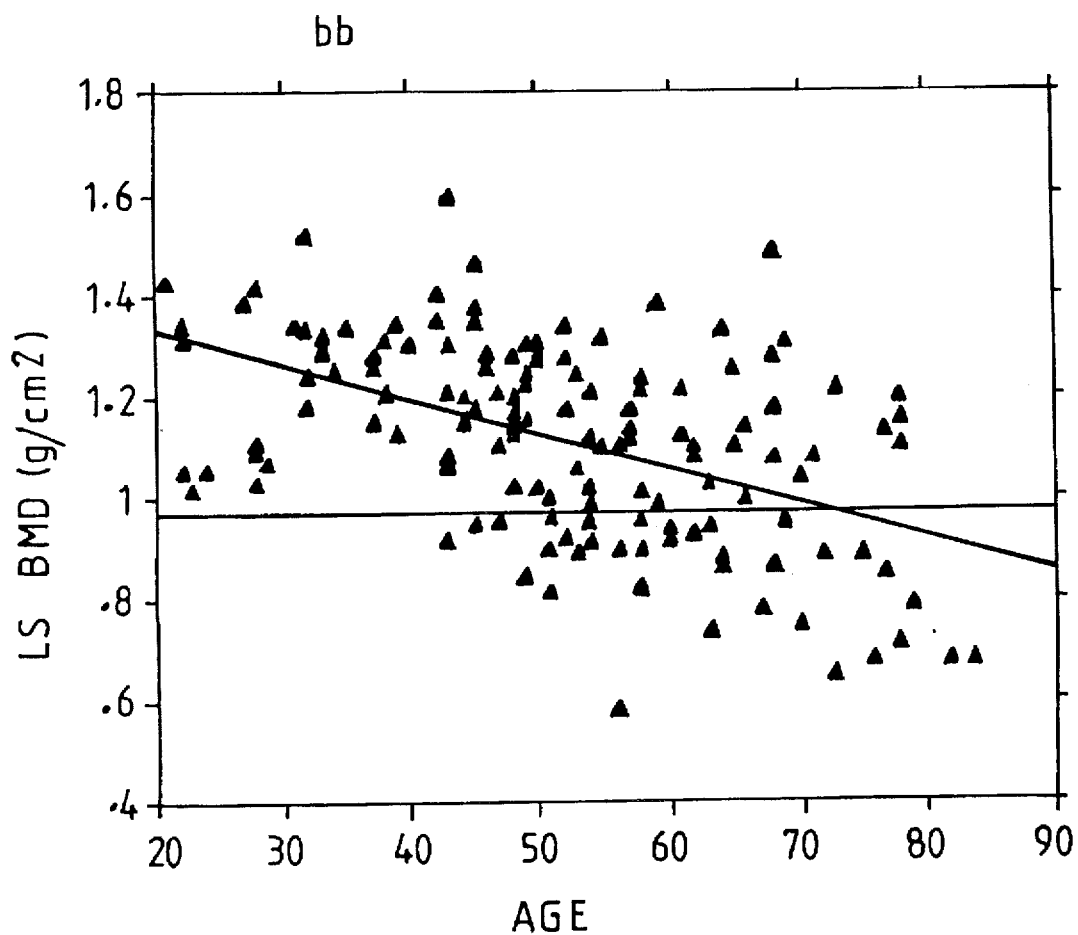
Figure 6A:
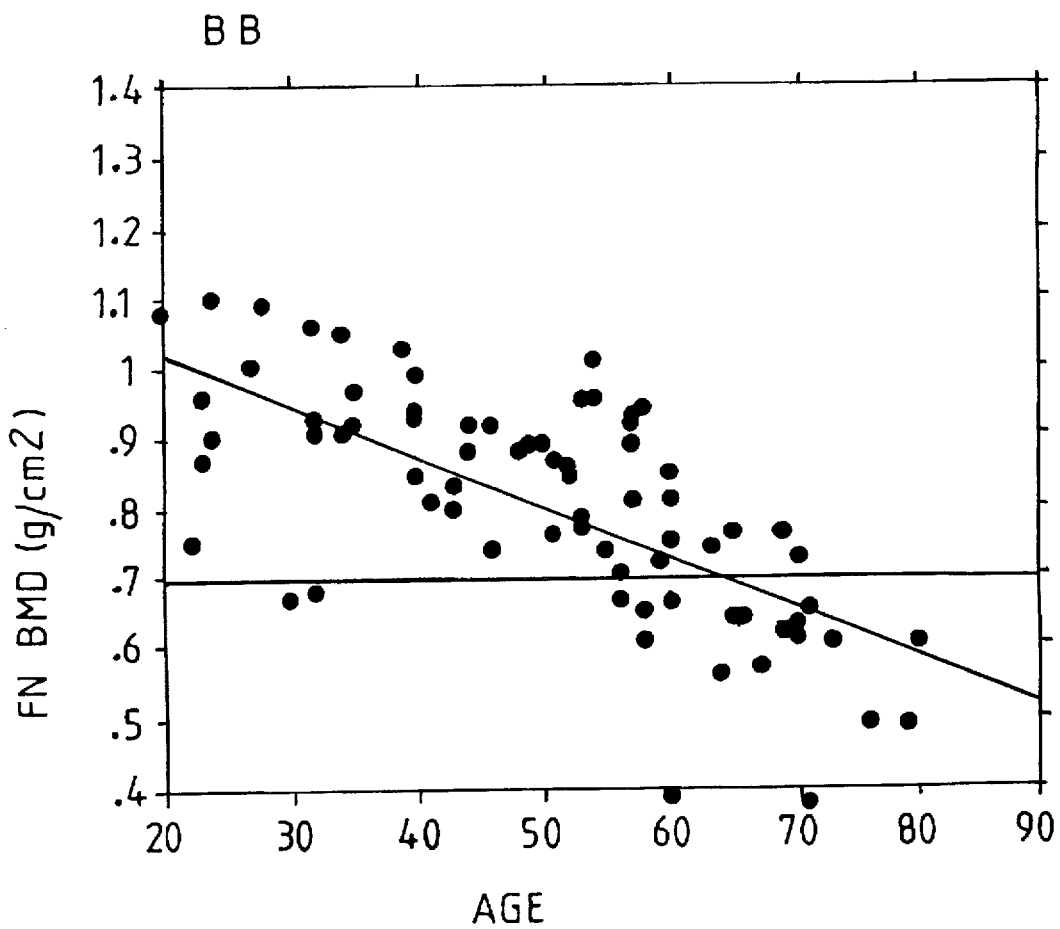
FIG. 6 shows age related regression of femoral neck bone mineral density and intersection with the fracture threshold according to genotype.
Figure 6B:
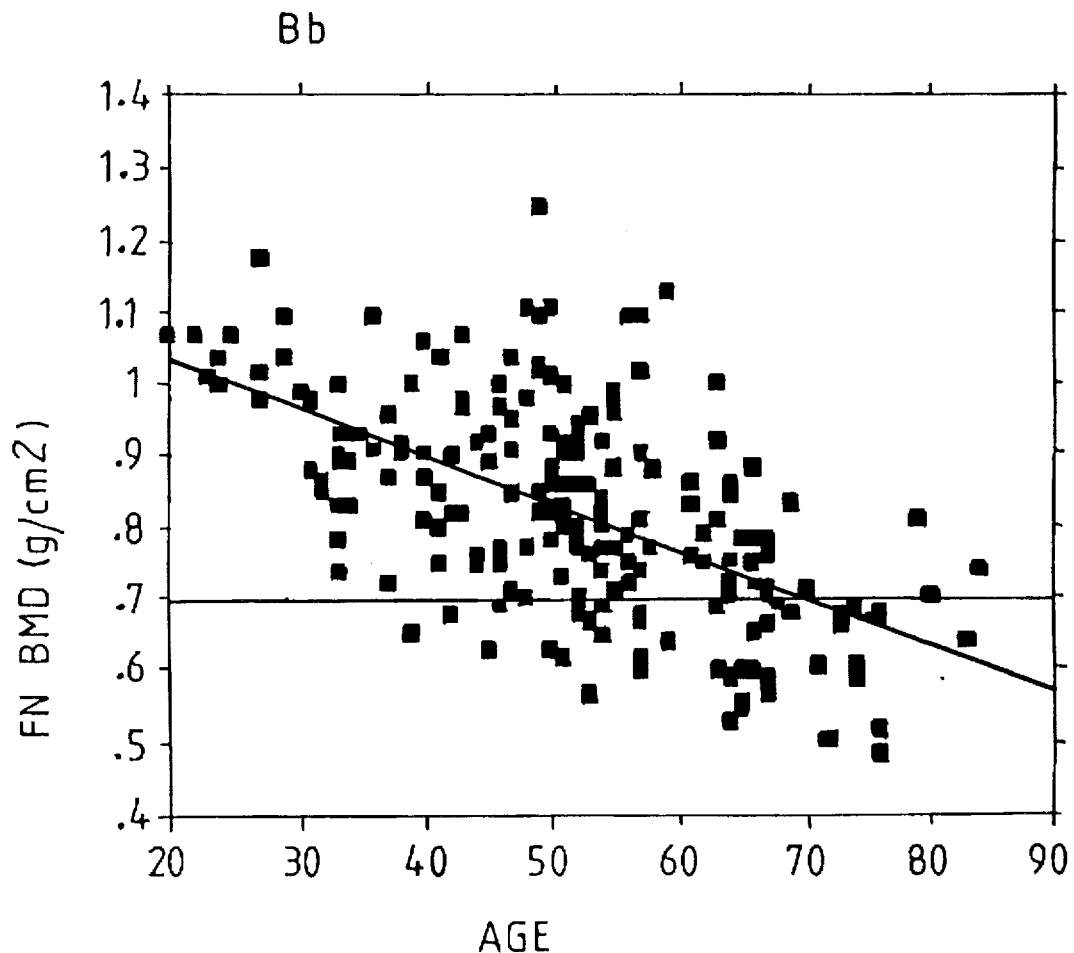
Figure 6C:
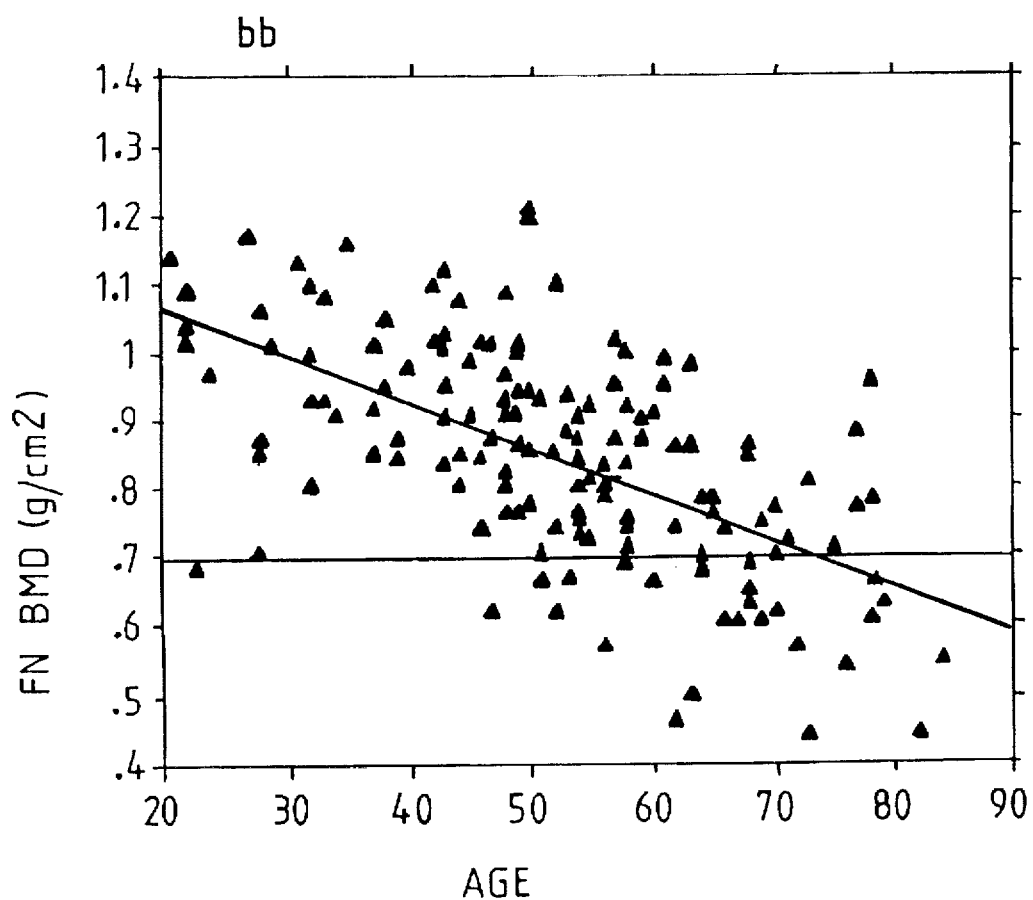
Figure 7A:
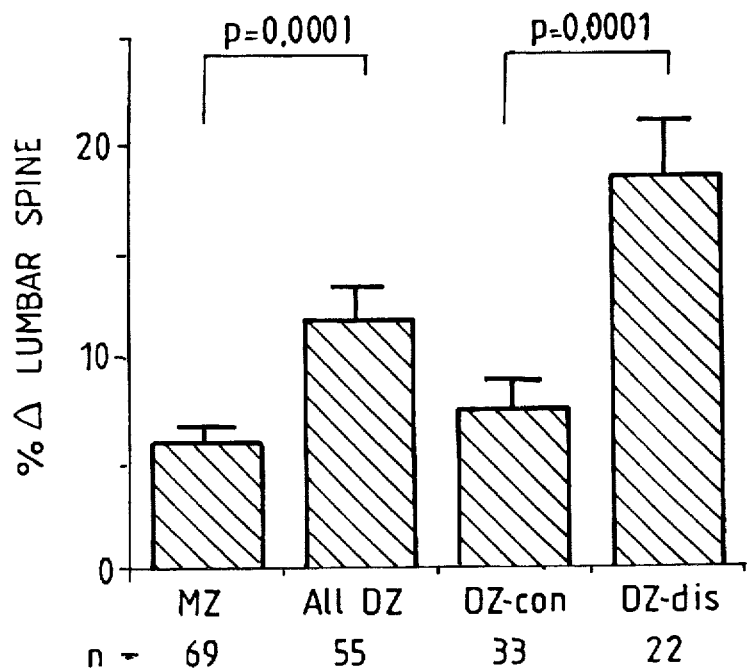
Figure 7B:
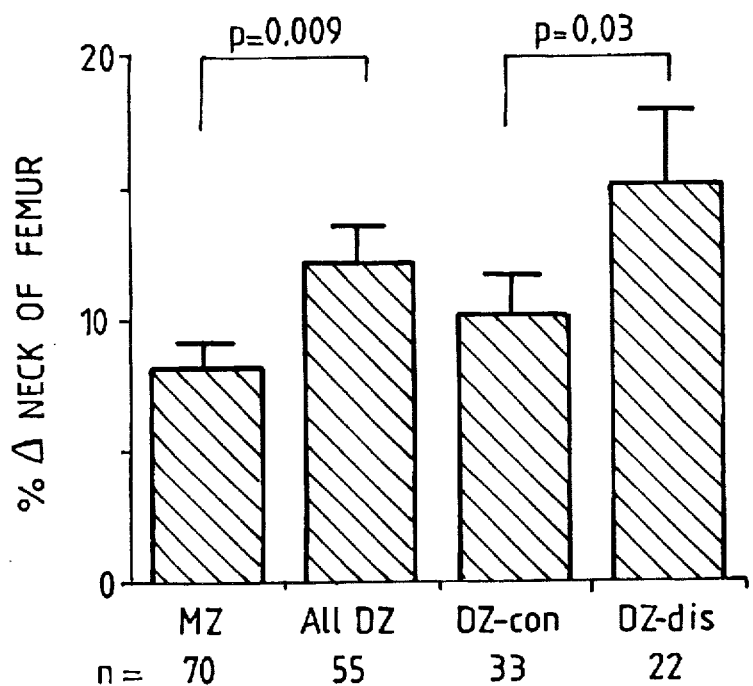
Figure 7C:
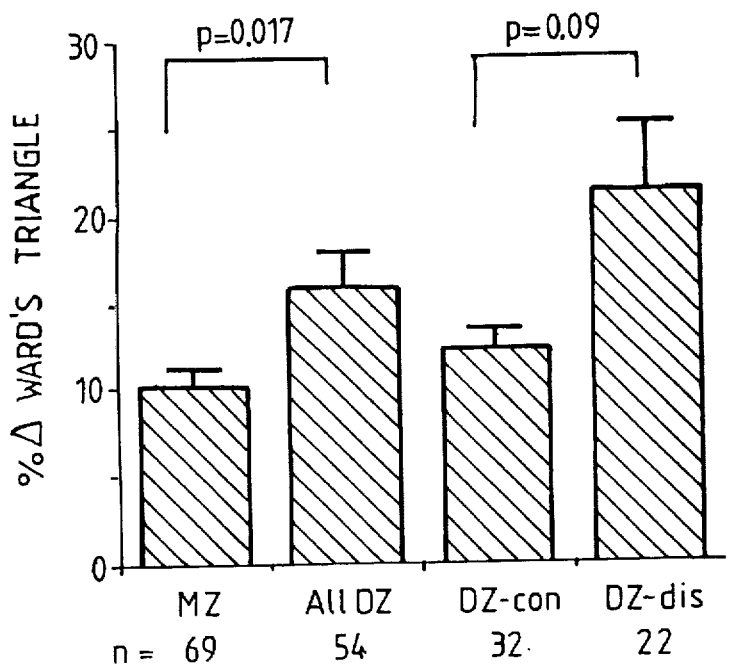
Figure 7D:
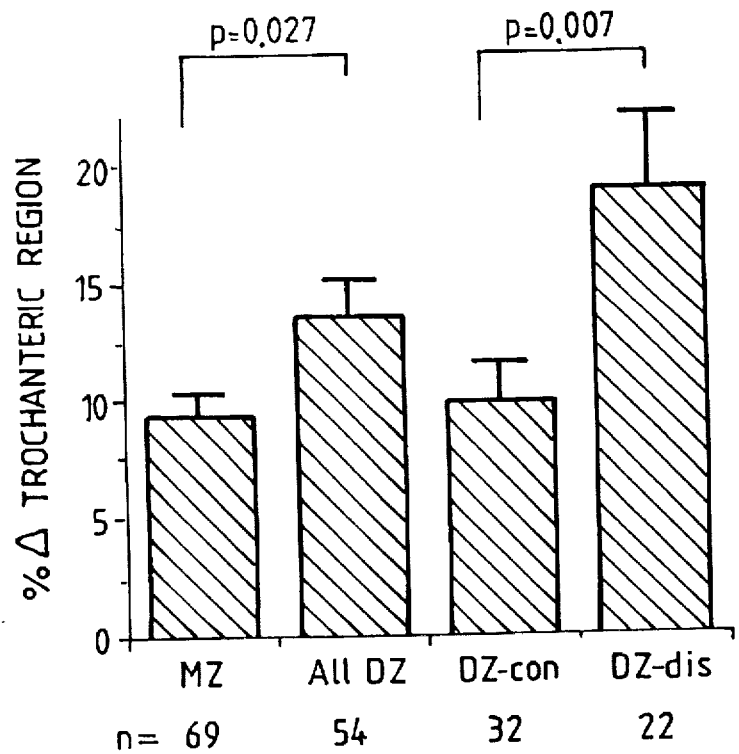
Figure 8A:
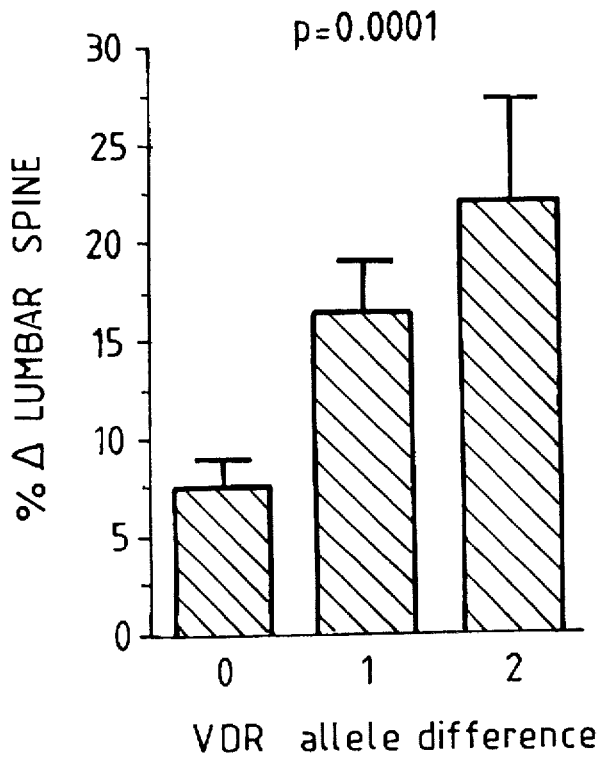
Figure 8B:
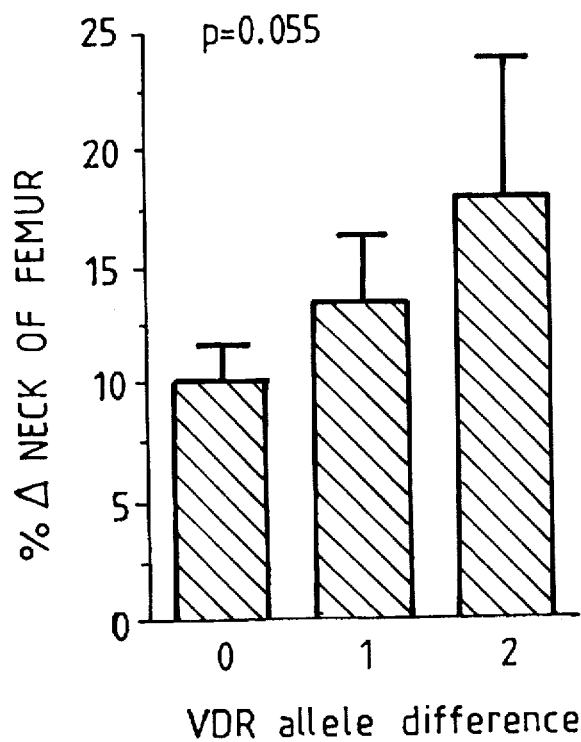
Figure 8C:
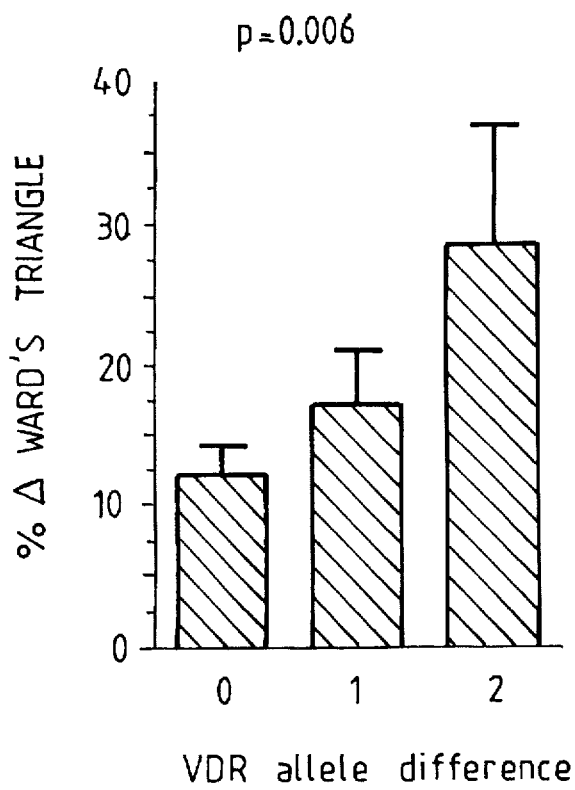
Figure 8D:
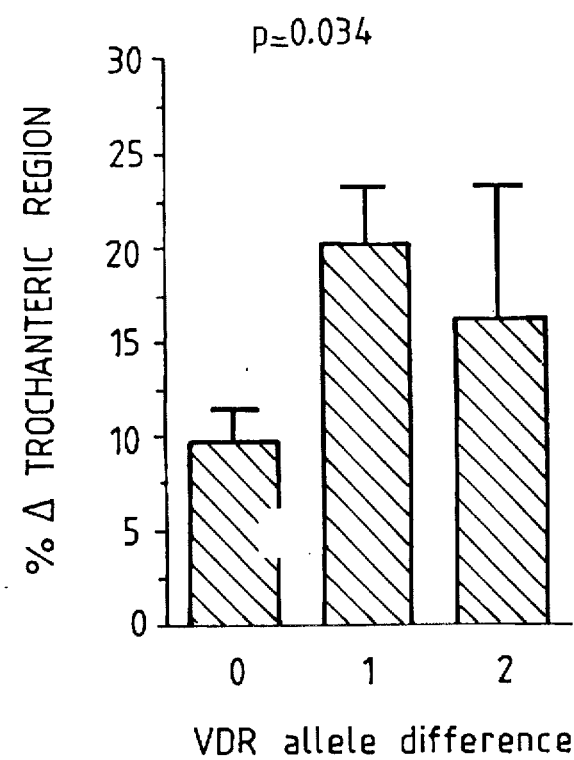

A value of lumbar spine BMD, below which a heightened risk of osteoporotic fracture exists, was derived form a large cross sectional study in the city of Dubbo Australia. This value 0.97 gm.cm$^2$ is similar to a fracture threshold described from an American population. Clearly, if VDR genotype affects BMD and subsequently osteoporosis susceptibility, a difference in the intercept of the age related change in bone mass and the fracture threshold should be apparent between genotypes. FIG. 5 shows simple age related regression lines for female LS BMD of BB, Bb and bb genotypes intersecting the fracture threshold value. A comparison between BB and bb reveals a 10 year difference in the intercept (60.3 yr versus 71.1 year, respectively) with an intermediate value for the Bb heterozygotes (68.1 year). A similar result was apparent for the neck of femur (FIG. 6) using a fracture threshold of 0.7 gm/cm$^2$ (BB, 66 years; Bb, 70 years; bb, 74 years).

STUDY 3

The effect of the common VDR gene alleles on bone density was examined using the twin model, in which within-pair comparisons eliminate age and various cohort confounders. 250 Caucasian twins were studied comprising 70 MZ and 55 DZ twin pairs, including 7 male MZ pairs and 6 male DZ pairs, aged between 17 and 70 years; MZ 45±13 yrs and DZ 44±11 yrs, mean±SD. Bone density was measured at the lumbar spine and proximal femur with a Lunar DP3 dual-photon absorptiometer (LUNAR Corporation, Madison, Wis.) or Lunar DEXA dual energy X-ray absorptiometry as previously described (Pocock et al 1987). All female twin pairs were concordant for menopausal status and if post menopausal, for years since menopause.

The VDR gene in the region bearing the polymorphic sites for the Bsm-1, Apa-1 and EcoRV sites previously shown to predict differences in bone turnover markers was sequenced. These sites are in the region of the gene from exon 7 to the 3'-UTR. None of the polymorphic sites was in the coding region or involved potential splice sites and the highly informative Bsm-1 site was found to arise from a G for A substitution in intron 8. There was only one difference in the coding region between the two most common allelic forms. This included a T for C substitution in exon 9, changing ATT to ATC, without changing the encoded amino acid sequence (isoleucine). The DNA sequence flanking the Bsm-1 site was used in a polymerase chain reaction-based method to amplify a 2.1–2.2 kb fragment from exon 7 to exon 9 to facilitate genotyping of subjects. PCR amplification of leucocyte DNA was performed with a Corbett FTS-1 Thermal Sequencer (Corbett Research, Mortlake NSW, Australia) PCR instrument using primers 5'-CAACCAAGACTACAAGTACCGCGTCAGTGA-3' and 5'-AACCAGCGGGAAGAGGTCAAGGG-3' prior to endonuclease digestion with Bsm-1 (New England Biolabs Inc, Gene Search, Brisbane, Australia). The presence of the Bsm-1 site cuts a 825 bp product to 650 bp and 175 bp fragments. A 4.7 kb plasmid with a single Bsm-1 site, which linearises with Bsm-1 digestion, was used as an internal control to avoid misassignment of the allelic forms due to partial digests.

Figure 9A:
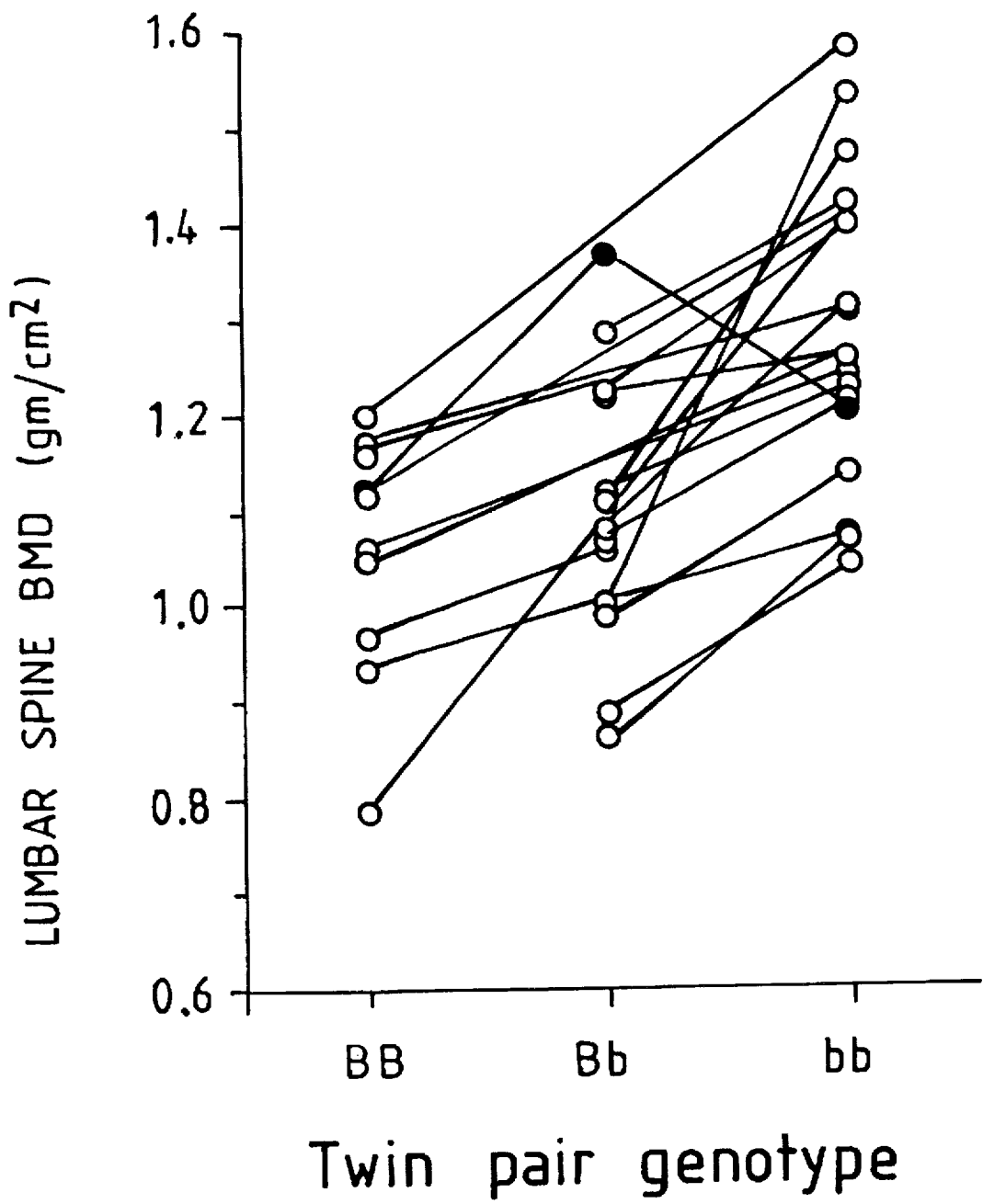
Figure 9B:
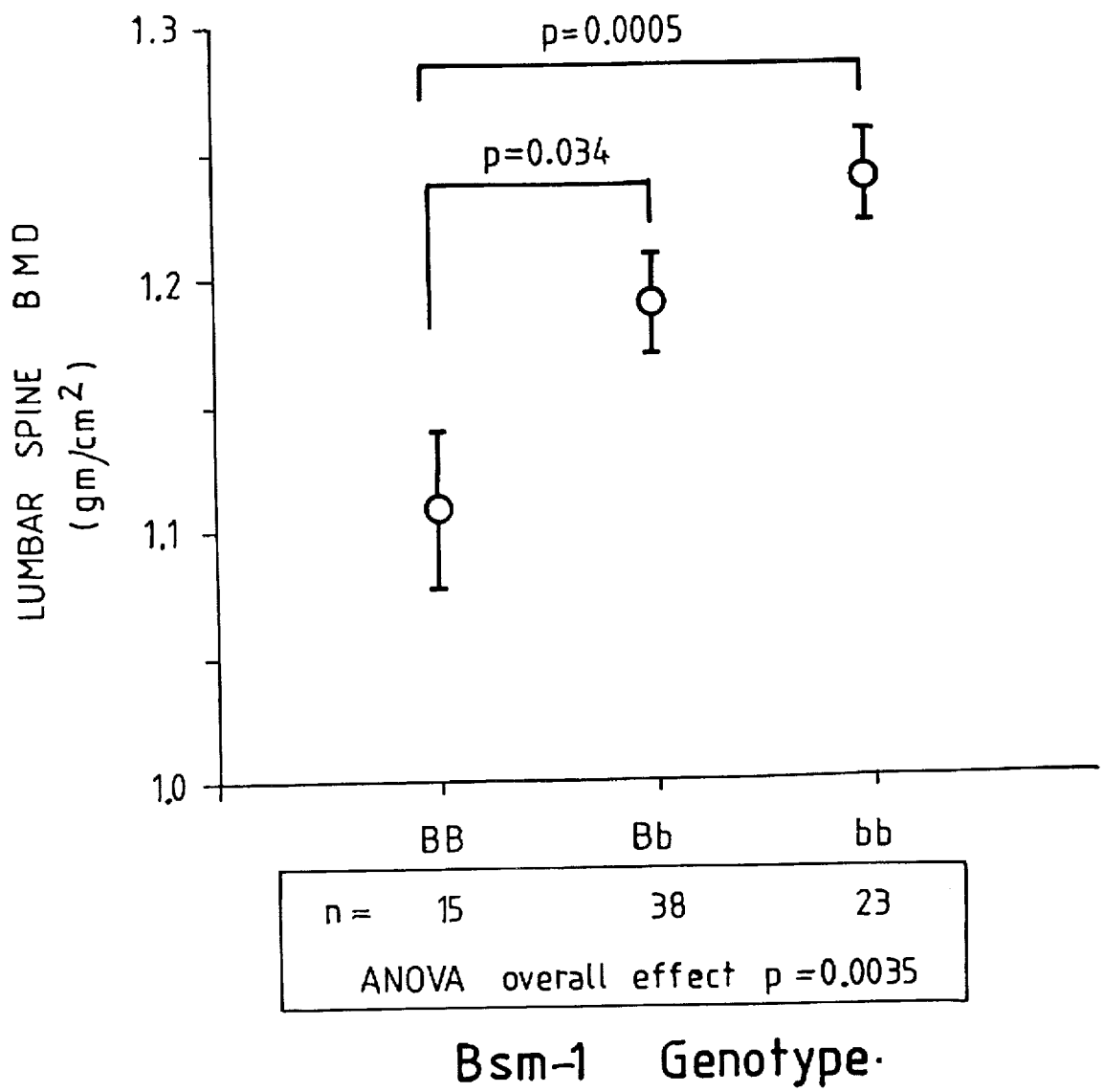

From twin studies the within pair difference in BMD (ΔBMD %) at the lumbar spine and proximal femur was examined in relation to allelic variation in DZ twin pairs (FIG. 7). In both regions this was significantly less in DZ twins concordant compared to those discordant for VDR gene alleles. The ΔBMD % for lumbar spine in the MZ twins was not significantly different from that in the DZ twins concordant for the VDR alleles, both of which were statistically different from those in DZ twins discordant for the alleles (p<0.0001). Similar but weaker effects in the proximal femur are consistent with stronger environmental influences on bone density in this region. Limiting the analysis to premenopausal twins did not alter the results. Controlling for potential confounding by anthropomorphic features of height and weight, VDR genotype remained the strongest predictor at the lumbar spine (p=0.0002) and the trochanteric region (p=0.02) although not at the neck region of the proximal femur. In view of the previously demonstrated co-dominant effect of Bsm-1 alleles on bone turnover indices, we would expect a co-dominant effect on the bone mass trait with a linear relationship between the degree of difference in genotype and the difference in trait within twin pairs (FIG. 8). According to the sib-pair linkage analysis approach, a significant correlation between the squared difference in a trait and the proportion of identical genes within a sibling pair indicates genetic linkage. By this analysis the VDR gene alleles were co-dominant at the lumbar spine and most sites in the proximal femur. Comparing the Δ BMD % with respect to degree of concordance for VDR alleles showed 1.5 to 2.5-fold greater within pair differences for the discordant twins (see FIGS. 7 and 8). In 21 of 22 dizygotic twin pairs discordant for the VDR alleles, the b allele was associated with higher bone density (FIG. 9A). In premenopausal females (randomly selected as singletons from MZ and DZ twin pairs), the VDR bb genotype was also associated with higher bone density (FIG. 9B) while the BB genotype was associated with lower bone mass with a clear codominant effect between the alleles (FIG. 9B).

These data demonstrate that the differences of VDR gene alleles indicate a major proportion of the differences in bone density in a population of normal individuals. The BB,AA, EE and/or tt VDR genotypes are associated with low BMD in both females and males. VDR gene RFLPs genotypes are therefore useful predictors of propensity to high bone turnover and low bone mass, physiological variability not only in peak bone mass but also bone mass in later life in both females and males. Until now, the mechanisms of the genetic effects on bone density and bone turnover have been unclear. However, 1,25-dihydroxyvitamin D is a enhancer of osteocalcin synthesis through the vitamin D responsive element in the promotor of the VDR gene (Morrison 1989 Science). The present inventors have also shown that common allelic variants of the VDR gene are associated with differences in the serum osteocalcin levels. Moreover, these allelic variants of the VDR gene predict the difference in bone density between dizygotic twin pairs.

It is concluded that these VDR gene RFLP's are markers for physiological variability in bone mass in both females and males. The present inventors have found that Bsm1 RFLP correlated independently with BMD at LS and FN.

TABLE 10

Age and years since menopause (YSM) amongst twins. A, those DZ twins concordant and discordant for VDR gene alleles; B; individuals with differing alleles for the VDR gene. All values are expressed as means ± SD.

A

|  | Concordant | Discordant |
|---|---|---|
| Age | 41.1 ± 10.6 | 45.5 ± 12.3 |
|  | n = 30 | n = 23 |
| YSM | 4.4 ± 3.6 | 9.3 ± 5.3 |
|  | n = 5 | n = 7 |

B

|  | BB | Bb | bb |
|---|---|---|---|
| Age | 44.0 ± 12.8 | 43.6 ± 13.4 | 45.7 ± 11.3 |
| YSM | 9.0 ± 2.5 | 11.8 ± 9.5 | 9.8 ± 7.8 |
|  | n = 9 | n = 12 | n = 7 |

TABLE 11A

Correlation co-efficients between monozygotic and dizygotic twin pairs with dizygotic pairs further segregated into those concordant and discordant for vitamin D receptor genotype.

| Variable | rMZ | rDZ | p | rDZ concordant | rDZ discordant | p |
|---|---|---|---|---|---|---|
| Lumbar Spine | 0.81 | 0.16 | <0.0001 | 0.41 | 0.04 | <0.001 |
| Femoral Neck | 0.79 | 0.43 | <0.0008 | 0.44 | 0.41 | NS |
| Ward's Triangle | 0.83 | 0.51 | <0.004 | 0.43 | 0.54 | NS |
| Trochanteric | 0.82 | 0.34 | <0.0002 | 0.49 | 0.38 | <0.006 |
| Weight | 0.80 | 0.42 | <0.0004 | 0.36 | 0.45 | NS |

Notes:
p; denotes the p value for the test that correlation coefficients are significantly different. In the twin model a significant difference between rMZ and rDZ is evidence for a genetic effect on the trait in question. In our comparison of DZ twin pairs with the same within-pair VDR genotype (DZ-concordant) or different within-pair VDR genotype (DZ-discordant), a significantly different correlation between rDZ-concordant and rDZ-discordant is supportive of a contribution of the VDR genotype to the genetic effect on the trait in question.

TABLE 11B

Within-twin pair proportional difference in bone mineral density according to zygosity and degree of discordance of the twin pair of alleles of the vitamin D receptor gene. Values of percentage differences are means ± sem.

| Variable | n | Lumbar spine | Femoral Neck | Ward's Triangle | Trochanteric region |
|---|---|---|---|---|---|
| MZ | 69 | 6.0 ± 0.7 | 8.1 ± 0.9 | 10.0 ± 1.2 | 9.3 ± 1.0 |
| DZ-all | 55 | 11.9 ± 1.4 | 12.1 ± 1.4 | 15.9 ± 2.0 | 13.5 ± 1.7 |
| DZ-concordant | 33 | 7.5 ± 1.3 | 10.2 ± 1.5 | 12.4 ± 2.0 | 9.7 ± 1.7 |
| DZ-discordant | 22 | 18.5 ± 2.5 | 15.1 ± 2.8 | 20.6 ± 3.8 | 18.7 ± 3.0 |
| Genetic effect DZ-discordant: | | 75% | 48% | 59% | 90% |
| −1 allele | 14 | 15.6 ± 2.5 | 13.2 ± 2.7 | 16.4 ± 3.7 | 19.9 ± 2.8 |
| −2 alleles | 8 | 22.0 ± 5.2 | 17.9 ± 5.9 | 28.5 ± 8.2 | 16.4 ± 7.0 |
| DZ-discordant/ DZ-con | | 2.47 | 1.48 | 1.66 | 1.93 |
| DZ-2 alleles/ DZ-con | | 2.93 | 1.75 | 2.30 | 1.71 |

Importantly, the homozygous BBAA or AAtt genotype are associated with low bone density, and mean BMD at the LS and FN site were about 12% and 8% lower in BBAA homozygotes compared with bbaa genotype in both females and males. These genotypic differences are important for later life, because these differences of BMD indicate a 10 year difference in the fracture threshold. These allelic differences provide a mechanism for the genetic effect on bone mass observed in twin studies and provide a simple genetic test of carrier status for low bone mass alleles. Identification of the vitamin D receptor genotype as an important determinant of bone mass may open new avenues for prevention and therapy for osteoporosis.

Demonstration of Differences in Response to Treatment in Different Gene Types.

Data described above have demonstrated that the VDR alleles described above are functionally different. It would therefore be expected that individuals of different genotype would exhibit different responses to treatment with calcitriol and/or analogues. This was confirmed by examining responses to calcitriol administration in 10 normal young females of each homozygous Bsm 1 genotype (BB and bb) and analysing responses to treatment in three markers of bone calcium metabolism; osteocalcin, parathyroid hormone and urinary calcium (see FIG. 10).

Osteocalcin serum levels were different (p<0.01) at basline in the BB and bb groups. The BB genotype again had the higher osteocalcin. After calcitriol treatment the bb group had a higher percent response from baseline than the BB group. Although the BB group had a lesser percent response, since they had a higher baseline osteocalcin, the total response was higher.

Parathyroid hormone is known to be repressed by calcitriol, however, the extent of repression by calcitriol treatment was significantly different in the two genotypic groups. Parathyroid hormone was weakly repressed in the BB group and strongly repressed in the bb group, indicating substantial differences in the response of PTH to calcitriol therapy. Total urinary calcium excretion over the treatment period (area under the curve) was significantly higher in the BB group than the bb group indicating different calcium handling responses according to genotype. the reduced repression of parathyroid hormone in the face of calcitriol treatment, coupled with increased urinary calcium output indicates different calcium homeostatic mechanisms, compatible with mobilisation of skeletal calcium. VDR and Other Conditions The vitamin D receptor and vitamin D endocrine system are implicated in several other pathological and physiological states. Such differences in the vitamin D receptor gene, leading to different responses to endogenous calcitriol, exogenous calcitriol and therapy using vitamin D analogues, will also result in differences in progression and susceptibility to other disorders where a significant component of regulation is effected by calcitriol. Known examples of conditions and diseases where the vitamin D endocrine system and VDR mediated events occur include AIDS virus (HIV-1) replication, breast cancer cell proliferation, colonic cancer cell growth, keratinocyte differentiation, psoriasis cell replication and function, spermatogenesis, melanoma and other tumours.

As a result of the invention described herein, it is therefore obvious that functionally different alleles of the VDR could affect the susceptibility, progress, prognosis and therapeutic efficacy of various treatments, in such diseases and conditions where the vitamin D receptor and vitamin D endocrine system are known to regulate aspects of the disease process. While these are examples of physiological and disease processes influenced by the vitamin D endocrine system, it is in no way exclusive of other processes influenced by the vitamin D endocrine system. Given the data described herein, it is obvious that all physiological and disease processes known to be influenced by the vitamin D endocrine system, as described in a recent comprehensive review by Walters, M. (newly identified actions of the vitamin D endocrine system; Endocrine reviews, 13:719–764) and papers referred to therein, could be assessed and investigated in the way described herein, and that these could be influenced by the vitamin D receptor genotype and therefore the genotype of an individual will be of importance to the prognosis, progression, susceptibility and treatment of all conditions and diseases in which vitamin D receptor and the vitamin D endocrine system are involved.

Irrespective of the physiological mechanism, these data have identified for the first time a gene involved in the regulation of bone density. Importantly the magnitude of the effect is such that it explains the majority of the strong genetic effect on bone density and indeed more than half of the adjusted population variation in bone density. These findings, which will allow earlier interventions in those at increased risk of osteoporosis, provide important insight into the mechanism of the wide population variance in bone density and open the way to development of novel specifically targeted therapies. This single gene with pleiotropic transcriptional activities is a model for many pathophysiological processes previously considered subject to complex multi-factorial genetic regulation.

This study describes a functional definition of naturally occurring alleles of a trans-acting transcriptional activator by correlation with the product of a target gene. The data also indicate that the receptor allelic differences also relate to major differences in a target organ—i.e., bone density. This method of genetic analysis provides a paradigm for the investigation of the functional significance of natural allelic variation within the genes of the ligand-activated receptor superfamily, which can contribute substantially to a more complete understanding of the steroid hormone endocrine system. It is also applicable to the genes for trans-acting regulators of all kinds.

Genotypic variations in transcriptional regulators of genes encoding regulatory and/or structural proteins, determine physiological set-points and predisposition to pathophysiological states with implications for susceptibility to disease and for determining likely responses to therapy. These genotypic variants are a general model for use in the determination of disease risk and for choice of therapy in prevention and treatment.

As a specific example of this model, allelic variants in the vitamin D receptor gene determine bone turnover, bone mass and sensitivity to environmental factors. As such these variants are markers of risk of development of osteoporosis and indicate likely response to various modalities of therapy.

The inventors have identified RFLP markers that define functionally different vitamin D receptor alleles. The RFLPs herein described are physical markers that are linked to genetic phenomena. The inventors advise that it is now obvious that any other RFLP, physical marker, polymorphic sequence, or genetic effect detectable in the vitamin D receptor gene or flanking DNA, which is in linkage with the currently defined markers, could provide the same information content as the markers herein described, dependent on the extent of linkage between the markers defined herein and any other such marker, consisting of RFLP, physical, polymorphic sequence, or genetic effect. The inventors thereby state that other markers, known or unknown, in linkage with the markers herein described, represent a claimed usage of this invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Haussler, M. R. (1986) Annu. Rev. Nutr. 6,527–562.
2. McDonnel, D. P. Mangelsdorf, D. J., Pike, J. W., Haussler, M. R. & O'Malley, B. W. (1987) Science 235, 1214–1217.
3. Baker, A. R., McDonnel, D. P., Hughes, M., Crisp, T. M., Mangelsdorf, D. J., Haussler, M. R., Pike, J. W., Shine, J. & O'Malley, B. W. (1988) Proc. Natl. Acad. Sci U.S.A. 85, 3294–3298.
4. Yamamoto, K. R. A. (1985) Annu. Rev. Genet. 19, 209–252.
5. Evans, R. M. (1988) Science 240, 889–895.
6. Marcelli, M., Tilley, W. D., Wilson, C. M., Griffen, J. E., Wilson, J. D. & McPhaul, M. J. ( 1990) Mol. Endocrinol. 4, (8), 1105–1116.
7. Hughes, M. R., Malloy, P. J., Kjeback, D. G., Kesterson, R. A., Pike, J. W., Feldman, D & O'Malley, B. W. (1988) Science 242, 1702–1705.
8. Lehrer, S., Sanchez, M., Song, H. K., Dalton, J., Levine, E., Savoretti, P., Thung, S. N. & Schachter, B. (1990) Lancet 355, 622–624.
11. Kelly, P. J., Hopper, J. L., Macaskill, G. T., Pocock, N. A., Sambrook, P. M. & Eisman, J. A. (1991) J. Clin. Endocrinol. Metab. 72, 808–813.

18. Faraco, J., Morrison, N. A., Shine, J. & Frossard, P. (1989) Nucleic Acids Res. 17, 2150.
19. Delmas, P. D., Stenner, D., Wahner, H. W., Mann, K. G. & Riggs, B. L. (1983) J. Clin. Invest. 71, 1316–1321.
20. Kelly, P. J., Pocock, N. A., Sambrook, P. N. & Eisman, J. A. (1989) J. Clin. Endocrinol. Metab 69, 1160–1165.
21. Catherwood, B. D., Marcus, R., Madvig, P. & Cheung, A. K. (1985) Bone 6, 9–13.
22. Pocock N. A., Eberl S., Eisman J. A., et al. Dual-photon bone densitometry in normal Australian women; a cross-sectional study. Med. J. Aust. 1987; 146:293-7.
23. Pocock N. A., Sambrook P. N., Hille N. et al. Assessment of spinal and femoral bone density by dual X-ray absorptiometry; comparison of lunar and hologic instruments. J. Bone. Min. Res. 1992; 7: 1081–4.
24. Maniatis, T., Fritsch, E. F. and Sambrook, J. (1981) Molecular Cloning: a laboratory manual Cold Spring Harbor Laboratory Press, Cold Spring Harbor, N.Y.

We claim:

1. A method of assessing an individual's predisposition to low or high bone density, development of high or low bone turnover and/or responsiveness to therapy for conditions relating to bone density or bone turnover comprising analyzing allelic variation in the vitamin D receptor gene of the individual, thereby determining an individual's predisposition to low or high bone density, development of high or low bone turnover and/or responsiveness to therapy for conditions relating to bone density or bone turnover.

2. A method as claimed in claim 1 in which the analysis comprises restriction fragment length polymorphism using endonuclease digestion.

3. A method as claimed in claim 2 in which a segment of the vitamin D receptor is amplified using polymerase chain reaction prior to endonuclease digestion.

4. A method as claimed in claim 2 in which the endonuclease is selected from the group consisting of Bsm1, Apa1, EcoRV, Taq1, and isoschizomers thereof.

5. A method as claimed in claim 4 in which the restriction endonuclease is Bsm1.

6. A method as claimed in any one of claims 3 to 5 in which the segment of the vitamin D receptor is amplified using a pair of primers selected from the group consisting of

5'-CAACCAAGACTACAAGTACCGCGTCAGTGA-3' (SEQ ID:NO 2)

and 5'-AACCAGCGGAAGAGGTCAAGGG-3' (SEQ ID:NO 3);

and 5'-CAGAGCATGGACAGGGAGCAAG-3' (SEQ ID:NO 4)

and 5'-GCAACTCCTCATGGCTGAGGTCTCA-3' (SEQ ID:NO 5).

7. A method as claimed in claim 1 in which the segment of the vitamin D receptor gene analysed represents a variableportion of the vitamin D receptor or gene regions in linkage with at least one of the Bsm1, Apa1, EcoRV and Taq1 cut sites.

* * * * *